United States Patent
Castro et al.

(10) Patent No.: US 11,890,751 B2
(45) Date of Patent: Feb. 6, 2024

(54) COMPACT SPHERICAL 3-DOF MECHANISM CONSTRUCTED WITH SCISSOR LINKAGES

(71) Applicant: Aalborg Universitet, Aalborg (DK)

(72) Inventors: Miguel Nobre Castro, Aalborg (DK); John Rasmussen, Aalborg (DK); Michael Skipper Andersen, Nørager (DK); Shaoping Bai, Aalborg (DK)

(73) Assignee: Aalborg Universitet, Aalborg (DK)

( * ) Notice: Subject to any disclaimer, the term of this patent is extended or adjusted under 35 U.S.C. 154(b) by 793 days.

(21) Appl. No.: 16/756,779

(22) PCT Filed: Oct. 17, 2018

(86) PCT No.: PCT/DK2018/050262
§ 371 (c)(1),
(2) Date: Apr. 16, 2020

(87) PCT Pub. No.: WO2019/076417
PCT Pub. Date: Apr. 25, 2019

(65) Prior Publication Data
US 2020/0238542 A1  Jul. 30, 2020

(30) Foreign Application Priority Data
Oct. 17, 2017 (DK) .......................... PA 2017 70789

(51) Int. Cl.
*B25J 18/00* (2006.01)
*A61B 34/30* (2016.01)
(Continued)

(52) U.S. Cl.
CPC ............ *B25J 18/005* (2013.01); *A61B 34/30* (2016.02); *A61B 90/50* (2016.02); *A61H 1/0281* (2013.01);
(Continued)

(58) Field of Classification Search
CPC ....... B25J 18/005; B25J 9/1065; B25J 9/0006
See application file for complete search history.

(56) References Cited

U.S. PATENT DOCUMENTS 7,144,326 B2    12/2006  Thompson
7,442,126 B2 *  10/2008  Thompson ................ F16D 3/30
                                            464/112
(Continued)

FOREIGN PATENT DOCUMENTS

DE    3133523 A1    4/1983
EP    1219754 A1    7/2002
(Continued)

OTHER PUBLICATIONS

Castro et al., "A compact 3-DOF shoulder mechanism constructed with scissors linkages for exoskeleton applications," *Mechanism and Machine Theory*, vol. 132, pp. 264-278, 2019.
(Continued)

*Primary Examiner* — Jake Cook
(74) *Attorney, Agent, or Firm* — Klarquist Sparkman, LLP

(57) ABSTRACT

A curved scissor linkage mechanism (1) includes at least four linkage elements (2) each having a first end (3) and a second end (4). The linkage elements are arranged to form sides of one or more rhombi or parallelograms. Each linkage element is rotationally connected to another linkage elements via a revolute joint (5) at the first end and is rotationally connected to another one of the other linkage elements via another revolute joint at the second end. The linkage elements are configured so that the axes of each joint coincide at one common remote centre of motion. The mechanism is connectable to a first external member (7) at a proximal end and is rotationally connectable to a second external member (9) at an opposite distal end to obtain three
(Continued)

DOFs. The scissor linkage mechanism may further include a motion controlling mechanism.

16 Claims, 16 Drawing Sheets

(51) Int. Cl.
    *A61B 90/50*     (2016.01)
    *A61H 1/02*     (2006.01)
    *A61H 3/00*     (2006.01)
    *B25J 9/00*     (2006.01)
    *F16H 21/54*     (2006.01)

(52) U.S. Cl.
    CPC .............. *A61H 3/00* (2013.01); *B25J 9/0006* (2013.01); *B25J 18/007* (2013.01); *F16H 21/54* (2013.01); *A61B 2034/305* (2016.02); *A61B 2090/506* (2016.02); *A61H 2201/1628* (2013.01); *A61H 2201/1676* (2013.01)

(56) References Cited

U.S. PATENT DOCUMENTS

| | | | |
|---|---|---|---|
| 8,747,236 B2* | 6/2014 | Pattakos | F16D 3/16 464/905 |
| 2015/0168179 A1 | 6/2015 | Bax et al. | |
| 2017/0189257 A1 | 7/2017 | Lan et al. | |

FOREIGN PATENT DOCUMENTS

| | | | |
|---|---|---|---|
| EP | 2150175 | B1 | 7/2014 |
| GB | 2161573 | A | 1/1986 |
| JP | 59115187 | A | 7/1984 |
| JP | 59156696 | | 9/1984 |
| JP | 2017064892 | A | 4/2017 |
| WO | WO 2008/031023 | A2 | 3/2008 |
| WO | WO 2008/031023 | A3 | 3/2008 |

OTHER PUBLICATIONS

International Search Report dated Jul. 24, 2020, issued by the European Patent Office in International Application No. PCT/DK2020/050110, filed Apr. 23, 2020, 5 pages.

Written Opinion of the International Searching Authority dated Jul. 24, 2020, issued by the European Patent Office in International Application No. PCT/DK2020/050110, filed Apr. 23, 2020, 10 pages.

International Search Report dated Dec. 20, 2018, issued by the European Patent Office in corresponding International Application No. PCT/DK2018/050262, filed Oct. 17, 2018, 4 pages.

Written Opinion dated Dec. 20, 2018, issued by the European Patent Office in corresponding International Application No. PCT/DK2018/050262, filed Oct. 17, 2018, 6 pages.

Christensen et al., "A Novel Shoulder Mechanism with a Double Parallelogram Linkage for Upper-Body Exoskeletons," *Wearable Robotics: Challenges and Trends*, Biosystems & Biorobotics 16, 2017, pp. 51-56, 6 pages.

Kocabas, "Gripper Design with Spherical Parallelogram Mechanism," Journal of Mechanical Design, vol. 131, Jul. 2009, 9 pages.

* cited by examiner

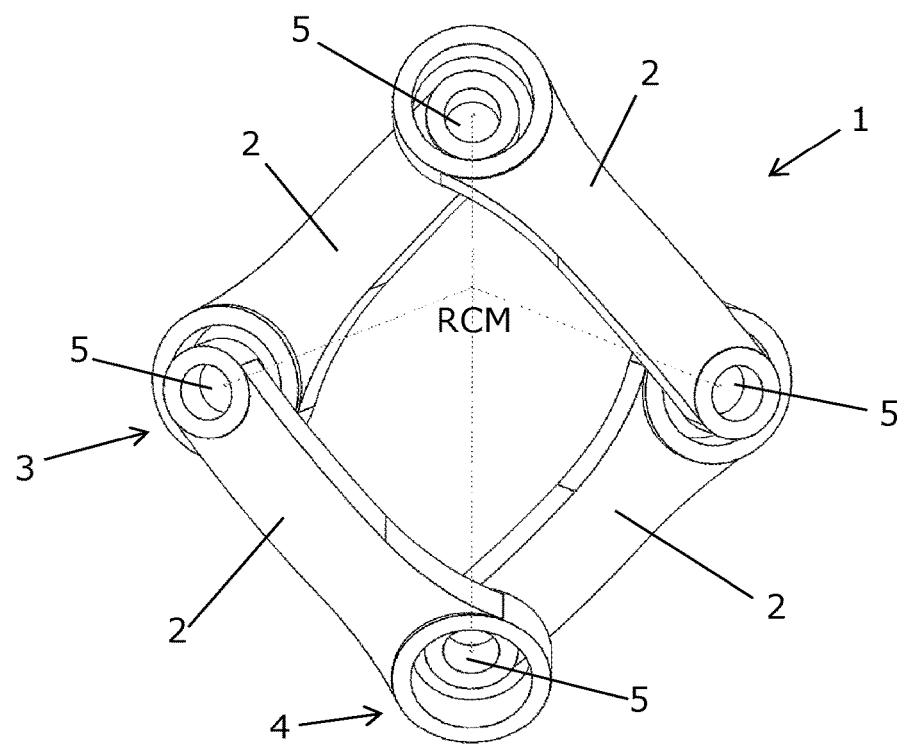
Fig. 1
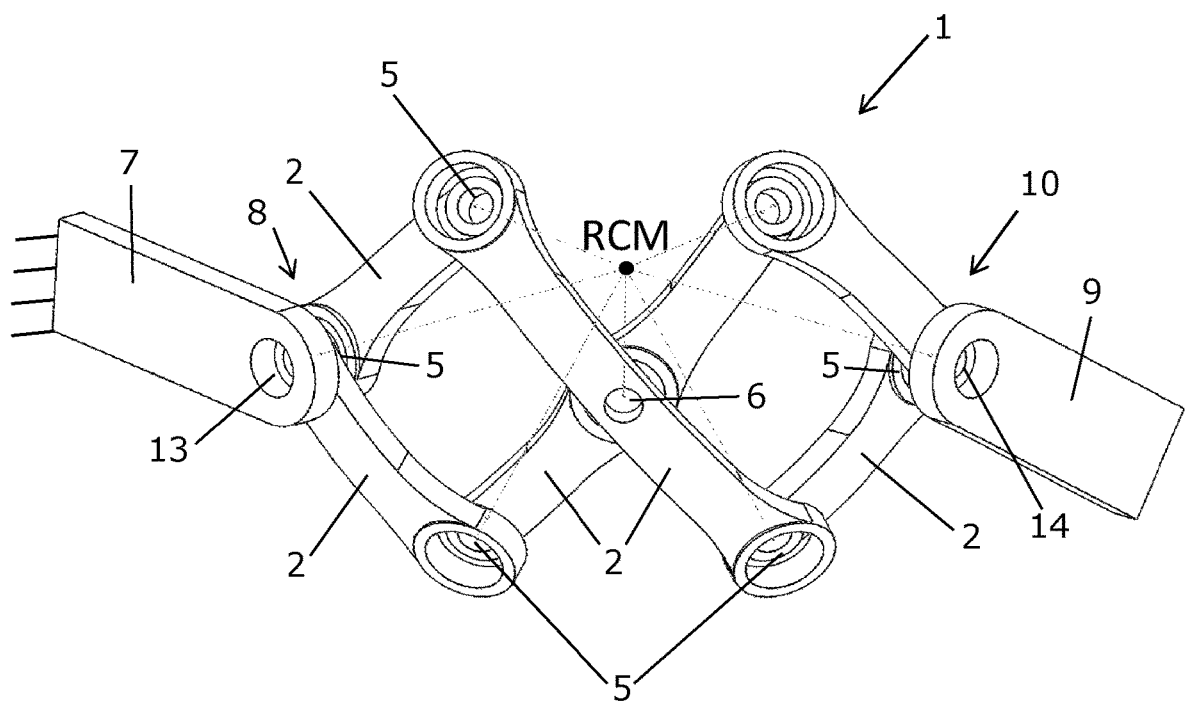
Fig. 2.a

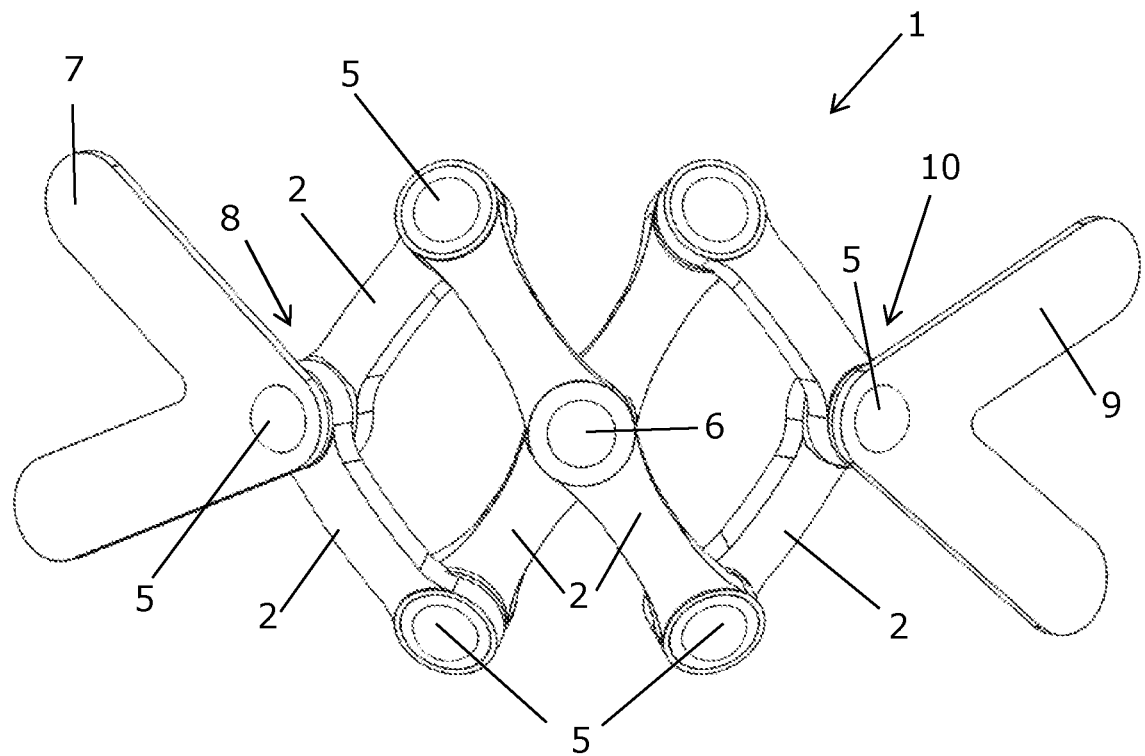
Fig. 2.b
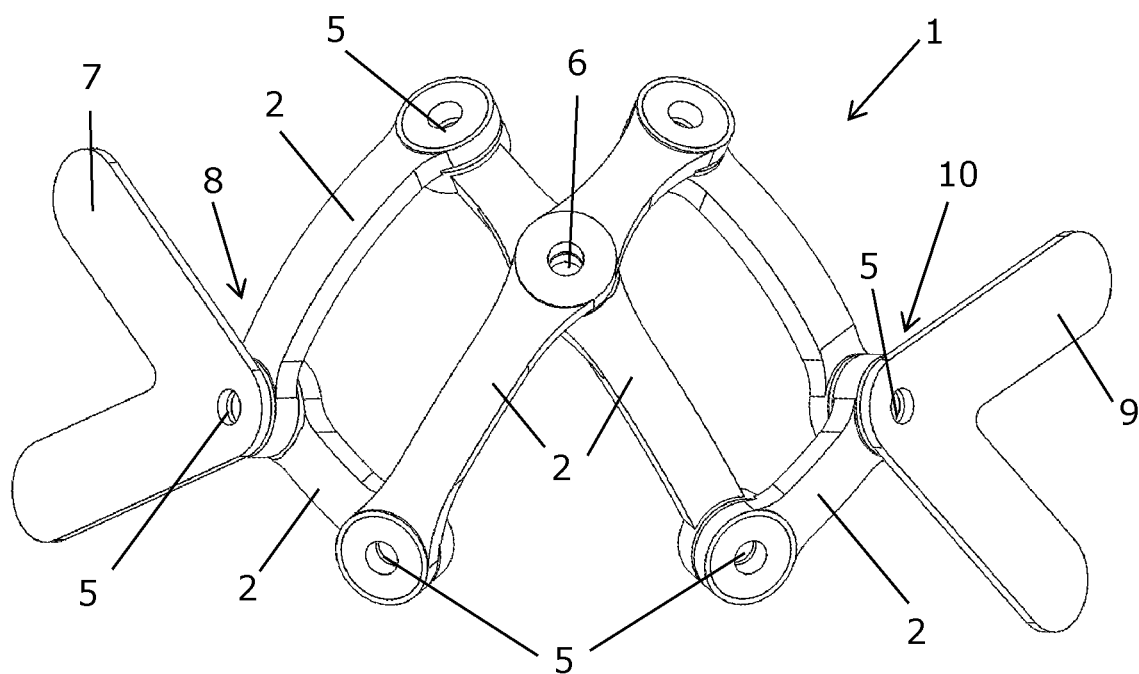
Fig. 2.c

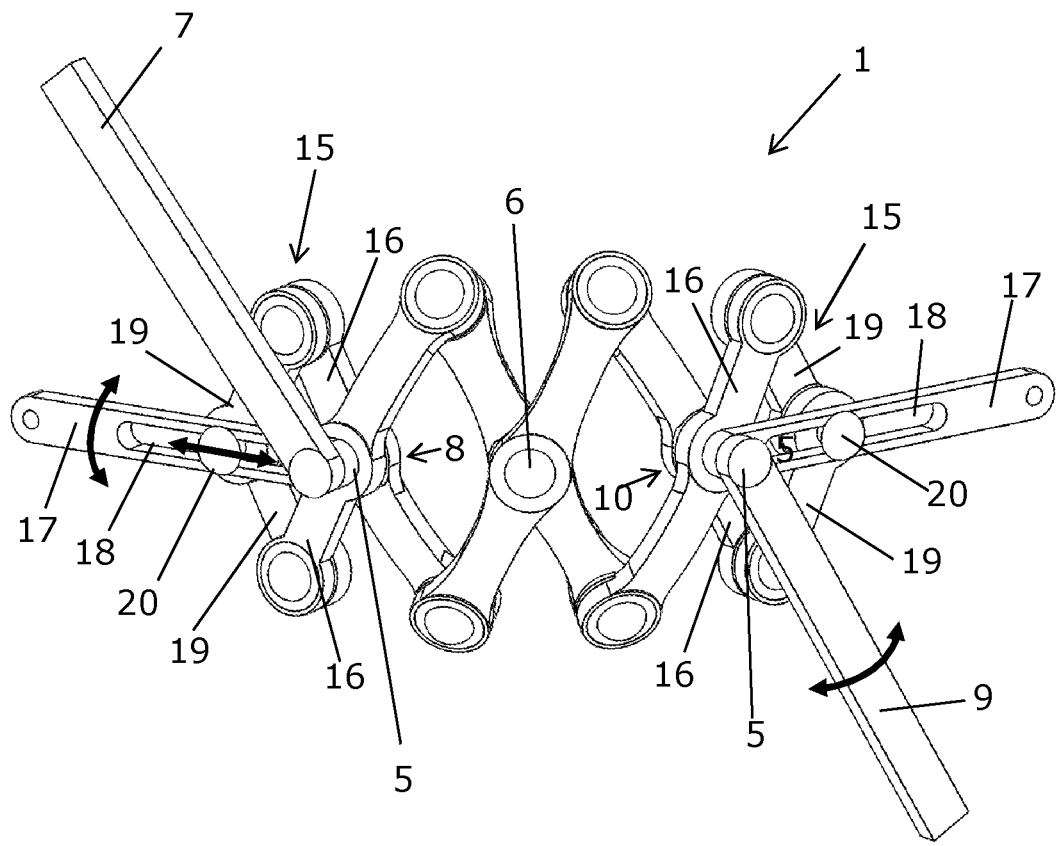
Fig. 10.a
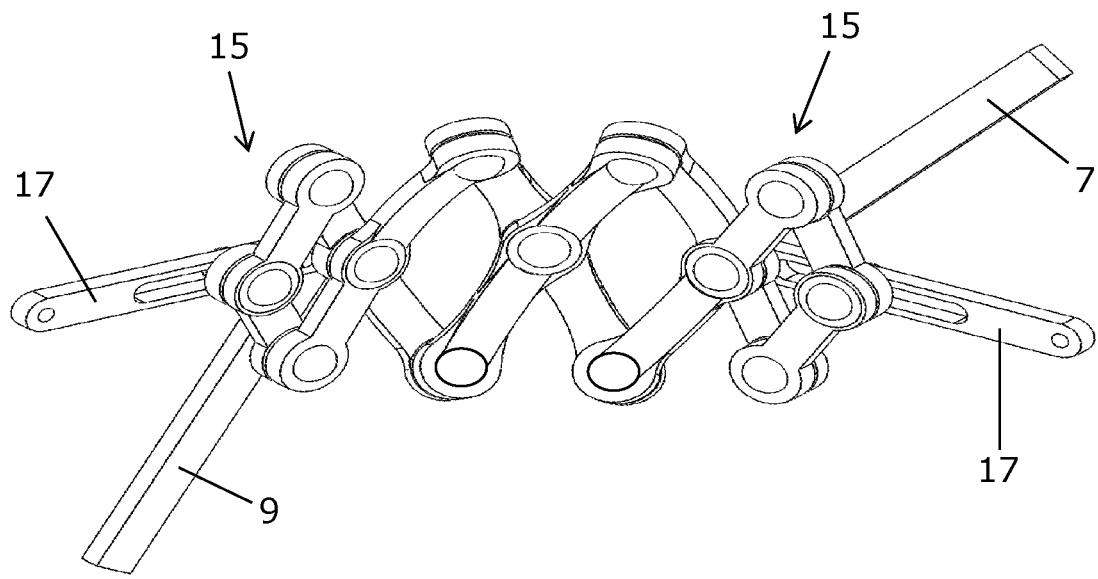
Fig. 10.b

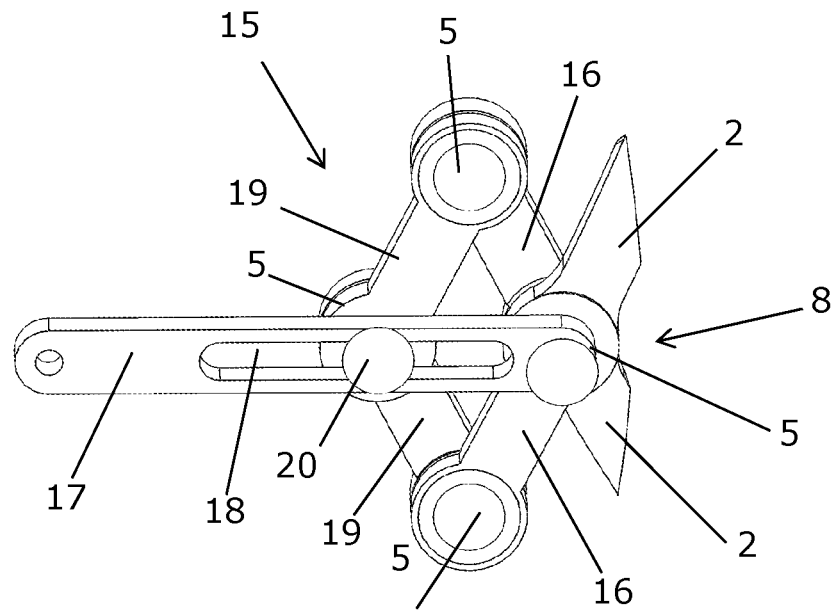
Fig. 11.b
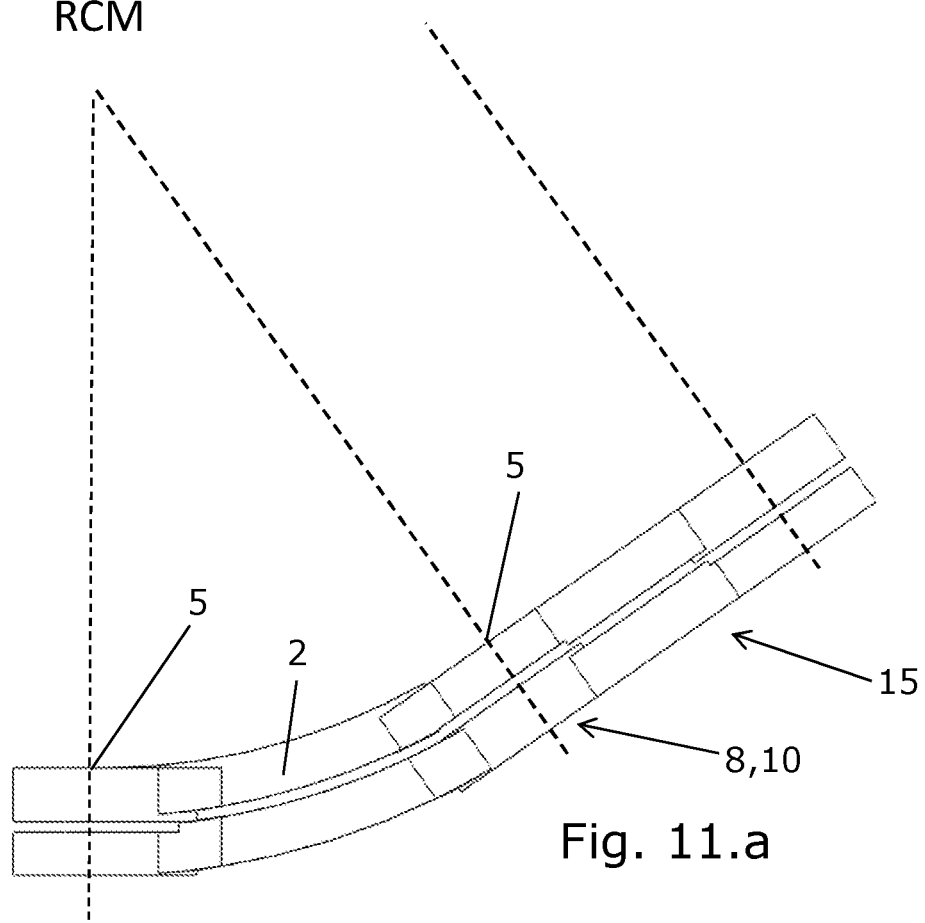
Fig. 11.a

COMPACT SPHERICAL 3-DOF MECHANISM CONSTRUCTED WITH SCISSOR LINKAGES

CROSS REFERENCE TO RELATED APPLICATIONS

This is the § 371 U.S. National Stage of International Application No. PCT/DK2018/050262, filed Oct. 17, 2018, which was published in English under PCT Article 21(2), which in turn claims the benefit of DK Application No. PA 2017 70789, filed Oct. 17, 2017, which is incorporated herein in its entirety.

FIELD OF THE INVENTION

The present invention relates to spherical linkage mechanisms and in particular to such mechanisms having three degrees-of-freedom.

BACKGROUND OF THE INVENTION

The need for spherical mechanisms and robotic spherical manipulators is increasing. The conventional industrial serial manipulators, composed of consecutive revolute joints, can work around an object but they often require a change of configuration when the robot approaches a singularity. The necessary reconfiguration of the straight links of these manipulators can be problematic, as it must simultaneously be ensured that the robot does not collide with objects. For this reason, the creation of serial spherical mechanisms with curved links is advantageous as they work on a spherical surface around the object. Most of the 3R spherical mechanisms are composed of three perpendicular rotational axes, thus behaving like a gimbal mechanism. An inherent disadvantage of this class of mechanisms is locking in inevitable singular configurations. This happens when the mechanism loses one degree-of-freedom (DOF) at a specific configuration, where two of the axes are aligned. This leads to indeterminacy, since a given rotation in that direction cannot be defined about one specific axis but simultaneously about two.

As result of the relevance of these spherical linkage mechanisms to various research areas, such as the biomedical engineering field, some improvements and workarounds were made in the past to avoid the complications related with singularity. Such solutions include the use of redundant linkages and design optimization on the lengths and consequently twist/centre angle of the linkages.

Spherical linkage mechanism are e.g. useful in relation to exoskeletons. An exoskeleton is a robotic device that is capable of producing supplementary muscular function of weakened body limbs. This enables the user to lift a greater load or compensate for a lack of strength. In exoskeleton designs, the mechanical structure of the exoskeleton has to duplicate the movements of the human skeleton joint to which it is connected remotely from the human body. Especially, complex joints of the human with more than one degree of freedom, such as the glenohumeral joint at the shoulder joint or the hip joint, can be described as a ball and socket joint. While building a shoulder joint of an exoskeleton, it is necessary to ensure that the linkage mechanism forming the shoulder joint can surround the anatomical shoulder structure while pairing with its motions and without intervening with the surrounding biological structures, such as bones, muscles and skin. On top of that, the joint centres of the person's shoulder and of the exoskeleton must be coincident to avoid discomfort.

Hence, an improved 3-DOF spherical linkage mechanism would be advantageous, and in particular, such a linkage mechanism which can be designed to be singularity-free in the anatomical shoulder joint workspace would be advantageous. Other applications of the mechanism itself should also be possible.

OBJECT OF THE INVENTION

It is an object of at least some embodiments of the present invention to provide a spherical linkage mechanism which has a more compact design than corresponding known linkage mechanisms providing three degrees-of-freedom.

It is another object of at least some embodiments of the present invention to provide a spherical linkage mechanism which is singularity-free within its practical range-of-motion when applied in the anatomical shoulder joint workspace of an exoskeleton.

It is another object of at least some embodiments of the present invention to provide a spherical joint mechanism which, when incorporated in an exoskeleton, makes it possible to replicate the three rotations in the shoulder joint without the exoskeleton colliding with the person wearing the exoskeleton.

It is another object of at least some embodiments of the present invention to provide a spherical joint mechanism which, when incorporated in an exoskeleton, makes it possible to obtain a geometrical structure wherein the parts follow the shape of the shoulder with significantly less protruding material when compared to prior art.

It is an object of some embodiments of the present invention to provide a spherical joint mechanism with which it is easier to control the movement thereof in a compact manner when compared to prior art mechanisms.

It is a further object of the present invention to provide an alternative to the prior art.

In particular, it may be seen as an object of the present invention to provide a linkage mechanism that solves the above-mentioned problems of the prior art.

SUMMARY OF THE INVENTION

Thus, the above described object and several other objects are intended to be obtained in a first aspect of the invention by providing a curved scissor linkage mechanism comprising at least four linkage elements each having a first end and a second end, the linkage elements being arranged to form sides of at least one rhombus or of at least one parallelogram, wherein:

the curved scissor linkage mechanism is extendable between a fully collapsed configuration and a fully extended configuration, each of the linkage elements:

is rotationally connected to at least one of the other linkage elements via a revolute joint at or near the first end and/or at least an intermediate point between the first end and the second end, and is rotationally connected to at least another one of the other linkage elements via another revolute joint at or near the second end and/or at an intermediate point between the first end and the second end, and the linkage elements are shaped, dimensioned and arranged so that the axes of all said revolute joints coincide at one common remote centre of motion (RCM), so that each of the linkage elements can move on the surface of an imaginary sphere having its centre at the common centre of motion, and the curved scissor linkage mechanism is grounded or connected or connectable to a first external member via a revolute joint with an axis which is coincident with that of the revolute joint between linkage elements arranged at a proximal end of the curved scissor linkage mechanism and is rotationally connected or connectable to a second external member via a revolute joint with an axis which is coincident with that of the revolute joint between linkage elements arranged at a distal end of the curved scissor linkage mechanism, the proximal and distal ends being located at opposite ends of the scissor linkage mechanism.

In embodiments having the linkage elements arranged to form the sides of parallelograms, it is preferred that there are at least two parallelograms to obtain the desired functionality of the scissor linkage mechanism.

The term "collapsed" refers to the situation where the curved scissor linkage mechanism in its most folded configuration for a given design. It does not necessarily mean that the linkage elements are as close to each other as what is shown in FIGS. 3.*a* and 3.*b*. Thus, the word "collapsed" could also be read to mean "folded" throughout the description of the invention.

The term "revolute joint" can also be referred to as a hinge joint. It is a one-degree-of-freedom kinematic pair often used in mechanisms. A revolute joint provides a single-axis rotation function used e.g. in folding mechanisms and other uniaxial rotation devices. The revolute joints in a curved scissor linkage mechanism according to the present invention may comprise bearings, shafts or bolts. A revolute joint axis can span one or more one-degree-of-freedom kinematic pairs if these are stacked along the very same axis.

By "grounded" is meant fixed in all six degrees-of-freedom to something else, such as a larger device which the scissor linkage mechanism forms part of or is to move in relation to. This larger device could e.g. be a part of an exoskeleton as will be explained below.

By "intermediate" is meant somewhere between the first and the second ends. It does not need to be a midpoint, but it can be so. This will be shown in the figures.

The curved scissor linkage mechanism may comprise a motion controlling mechanism which is arranged at the proximal end and/or at the distal end, and wherein for each motion controlling mechanism:

the linkage elements at the proximal end or the distal end, respectively, are mutually connected at intermediate points so that parts of these linkage elements extend away from the curved scissor linkage mechanism, the motion controlling mechanism comprises these extending parts of the linkage elements, and the movement of the curved scissor linkage mechanism can be controlled by moving the two extending parts of the linkage elements.

By "motion controlling mechanism" is meant an extension of the curved scissor linkage mechanism; the motion controlling mechanism is not intended to be used on its own but in combination with the other features of the invention as will be more clear from the figures and the description thereof.

In some embodiments of the invention, the motion controlling mechanism may further comprise:

a guiding member having a guide track, and two guide linkage members which are rotationally connected to each other and have a linkage mover arranged at the rotational connection between them, wherein each of the two guide linkage members rotationally connects one of the extending parts of the linkage elements to the linkage mover, and wherein the linkage mover is engaged with the guide track in such a way that the movement of the curved scissor linkage mechanism can be controlled by moving the linkage mover relative to the guide track, or by moving directly the two extending parts of the linkage elements at the proximal end and/or the distal end.

In alternative embodiments to be one just mentioned, the motion controlling mechanism may further comprises a linkage mover connected to at least one of the extending parts via a guide linkage member, the first or the second external member adjacent to the motion controlling mechanism comprises a guide track, and the linkage mover is engaged with the guide track in such a way that the movement of the curved scissor linkage mechanism can be controlled by moving the linkage mover in relation to the guide track.

A guide track may e.g. be slot or recess which is adapted to at least partly receive and thereby guide the linkage mover therein.

The guiding member may comprise further features, such as holes for attachment of cables used in the controlling of the scissor linkage mechanism.

The curved scissor linkage mechanism may comprise further features, such as additional linkage elements e.g. in the form of crossbars sub-dividing the at least one rhombus or the at least one parallelogram into sub-units.

The motion controlling mechanism may be planar or curved. When it is curved, it may have the same RCM as the curved scissor linkage mechanism. The motion controlling mechanism may be smaller or bigger than a rhombus of the scissor linkage mechanism e.g. due to limited space being available at the location where it is arranged given a particular application.

Is also possible within the scope of the present invention to control one or the two motion controlling mechanisms directly at the extending parts of the linkage elements on which controlling cables are attached without the presence of guide linkage members, without the linkage mover and without a guiding member.

When the curved scissor linkage mechanism is connected to both a first and a second external member as described above, the mechanism is a three-degrees-of-freedom mechanism. When it is only connected to an external member at the proximal end, it can be referred to as a two-degrees-of-freedom mechanism.

A mechanism as described above is also sometimes, and in particular within the robotics field, referred to as a "wrist" mechanism. The term is used to address robots or mechanisms capable of two or three degrees-of-freedom rotations about concurrent or perpendicular axes, respectively. When three axes are completely perpendicular to each other, the mechanism is often called a gimbal. The term "wrist" is used to resemble a human wrist even though a human wrist only has two degrees-of-freedom (flexion/extension and abduction/adduction) and the third rotation is considered as the forearm pronation/supination motion. The term "wrist" will be used in parts of the detailed description below.

The curved scissor linkage mechanism may further comprise a first connector for grounding or connecting the scissor linkage mechanism to the first external member and/or a second connector for rotationally connecting the scissor linkage mechanism to the second external member. Such first and second connectors can e.g. be a shaft, a bolt, a bearing or a rivet/pin.

In some embodiments of the invention, the curved scissor linkage mechanism may comprise at least six linkage elements arranged to form a series of at least two coherent rhombi, wherein:

each of the linkage elements located adjacent to a subsequent rhombus is shared by two neighbouring rhombi and has a longitudinal extension so that it forms sides of those two neighbouring rhombi, and neighbouring rhombi are rotationally connected via an intermediate revolute joint located between the first and second ends of the connected linkage elements forming sides of those rhombi. Such an embodiment having two coherent rhombi will be described in relation to the figures. With this embodiment, it is possible to reduce the surface space occupied by the mechanism compared to a mechanism with four linkage elements. Any number of rhombi will be covered by the scope of the present invention. The actual number to use for a given application depends on a number of parameters including the necessary spatial extension that the mechanism is to be movable across, and the spatial location of other neighbouring elements with which collision is to be avoided.

In alternative embodiments, the curved scissor linkage mechanism may comprise at least six linkage elements arranged to form a series of at least two coherent parallelograms, wherein:

each of the linkage elements located adjacent to a subsequent parallelogram is shared by two neighbouring parallelograms and has a longitudinal extension so that it forms sides of those two neighbouring parallelograms, and neighbouring parallelograms are rotationally connected via an intermediate revolute joint located between the first and second ends of the connected linkage elements forming sides of those parallelograms.

By "series" is meant that the linkage elements can be arranged to form a coherent pattern, such as a row or a network.

In presently preferred embodiments of the invention, all the linkage elements are curved. Hereby a very compact linkage mechanism is obtained. However, if desired for a given use, it will also be possible that the scissor linkage mechanism comprises linkage elements comprising straight sections whereby it is possible to reduce the space taken up on the outside of the mechanism by taking up more space on the inside. In embodiments wherein all the linkage elements are curved this may also be the case for the parts extending into the motion controlling mechanism, if present.

The linkage elements may be arranged in mutually overlapping relationships at the revolute joints in such a manner that the linkage elements are movable on two or more imaginary spherical surfaces having different radii of curvature. In alternative embodiments, the linkage elements are shaped, dimensioned and arranged in such a way at the first and second ends that all the linkage elements are movable on one common imaginary spherical surface with common remote center of motion. An example of such a design will be given in relation to the figures.

In some embodiments of the invention, the curved scissor linkage mechanism comprises at least two rhombi or parallelograms of different sizes. Hereby the mechanism can be optimised for a specific application depending on the desired ranges and types of motion.

The curved scissor linkage mechanism as described above may further comprise actuator means for activating the scissor linkage mechanism and either control means for controlling the actuator means or connectors in communication with external control means for controlling the actuator means. Such actuator means may e.g. form part of the external components to which the scissor linkage mechanism is connected. This can be applied to powered robots and active exoskeletons.

In a second aspect, the invention relates to an exoskeleton with a joint comprising a curved scissor linkage mechanism according to the first aspect of the invention. Such a joint may e.g. be a shoulder joint or a hip joint. The advantages of using a mechanism according to the invention for joints in an exoskeleton will be described in details in relation to the figures.

In a third aspect, the invention relates to a spherical coordinate positioning tool comprising a curved scissor linkage mechanism according to the first aspect of the invention. Such a spherical coordinate positioning tool may e.g. be a surgical tool. If desired for this or other applications, the invention also covers embodiments wherein not all the possible degrees-of-freedom of the mechanism itself are utilized during normal use of the mechanism. It may e.g. be possible to neglect one of the rotations at the ends of the mechanism allowing for the second external member to translate along that rotation axis if that is advantageous for that specific use as in the case of a surgical need or an extrusion head on a 3D-printer.

For some of the possible applications of the invention, it may be advantageous to use two or more independent curved scissor linkage mechanisms according to the invention. In relation to surgery, it could e.g. be advantageous for the surgeon to manipulate two or more needles or surgery instruments at the same time.

The invention according to the first aspect may find use in a number of other application including laser welding or cutting, solar disks, 3D printing, spray-painting machines, satellite disk housings, spherical manipulators, immersive VR environments, camera quality inspection, and haptic devices for training.

The first, second and third aspects of the present invention may each be combined with any of the other aspects. These and other aspects of the invention will be apparent from and elucidated with reference to the embodiments described hereinafter.

BRIEF DESCRIPTION OF THE FIGURES

The curved scissor linkage mechanism according to the invention will now be described in more detail with regard to the accompanying figures. The figures show one way of implementing the present invention and is not to be construed as being limiting to other possible embodiments falling within the scope of the attached claim set.

FIG. 1 shows schematically an embodiment of the invention having four linkage elements joined to form one rhombus.

FIG. 2 shows schematically embodiments of the invention having six linkage elements joined to form two coherent rhombi or parallelograms and first and second external members connected at the proximal and distal ends, respectively. FIGS. 2.a and 2.b show two different shapes of the first and second external members connected to a scissor linkage mechanism having the linkage elements forming two rhombi. FIG. 2.c shows an alternative scissor linkage mechanism having the linkage elements forming two parallelograms.

FIGS. 5.a and 5.b show front and back views, respectively. FIG. 5.c shows a lateral view of the inner and outer small linkages. FIG. 5.d shows a lateral view of the inner and outer large linkages.

FIG. 10 shows an embodiment of the invention comprising motion controlling mechanisms at both the proximal and distal ends.

FIG. 11.a shows schematically a top view of part of the mechanism in FIG. 10, and FIG. 11.b shows schematically a partial view of the motion controlling mechanism.

DETAILED DESCRIPTION OF AN EMBODIMENT

Figure 3:
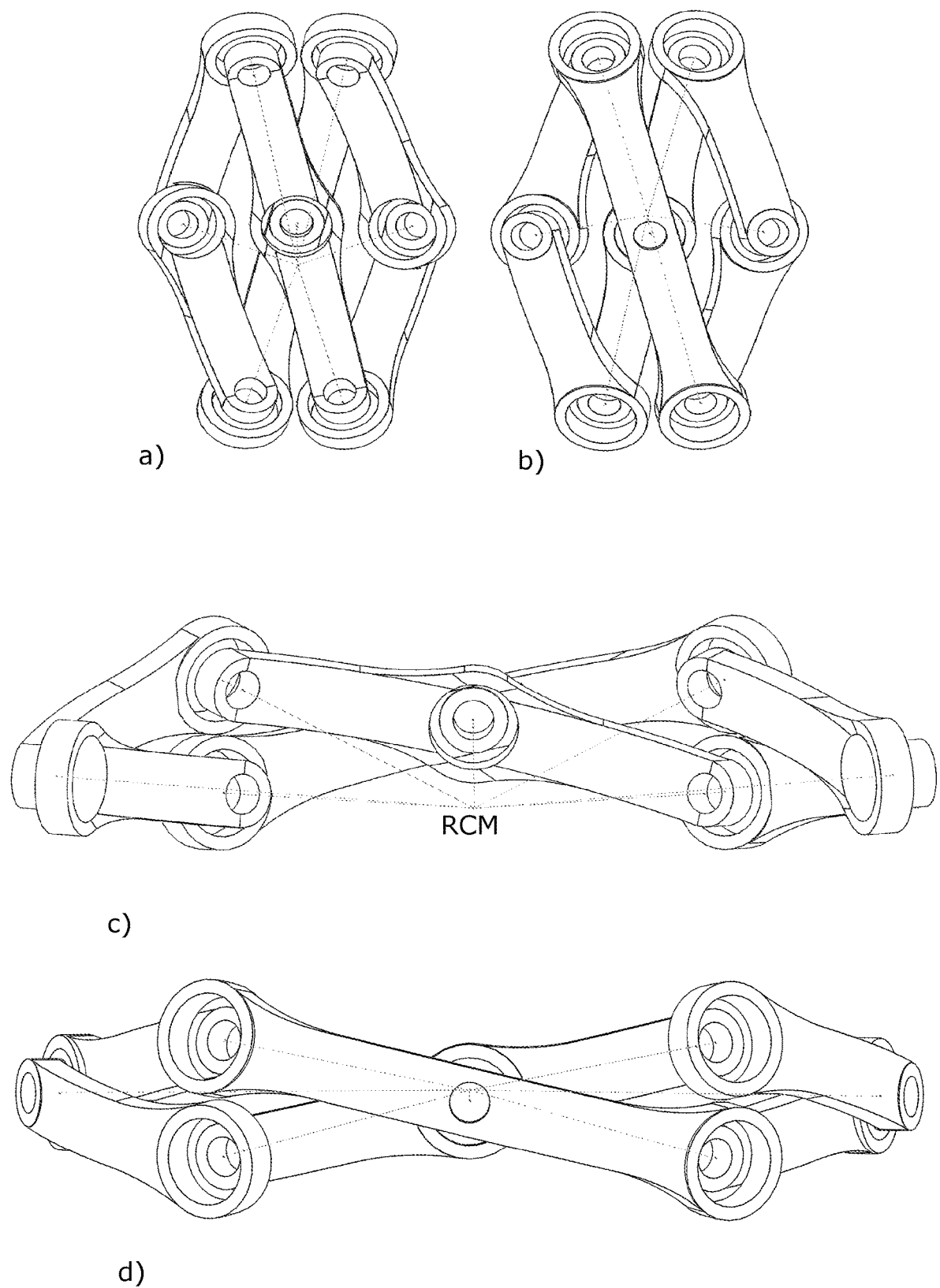
FIG. 3 shows schematically how a scissor linkage mechanism can be extended from a fully collapsed configuration (FIGS. 3.a and 3.b) to a fully extended configuration (FIGS. 3.c and 3.d).

FIG. 1 shows schematically a curved scissor linkage mechanism 1 according to the present invention. It has four linkage elements 2 each having a first end 3 and a second end 4, and the linkage elements 2 are arranged to form sides of a rhombus. Each of the linkage elements 2 is rotationally connected to one of the other linkage elements 2 via a revolute joint 5 at or near the first end 3 and is rotationally connected to another one of the other linkage elements 2 via another revolute joint 5 at or near the second end 4. In the figures, the revolute joints 5 are schematically shown without the components, such as shafts, bolts, or bearings, actually establishing the joining for illustrative purposes only.

Another embodiment of the invention is shown schematically in FIGS. 2.a and 2.b. This curved scissor linkage mechanism 1 has six linkage elements 2 arranged to form a series of two coherent rhombi. As shown, each of the linkage elements 2 located adjacent to a subsequent rhombus is shared by the two neighbouring rhombi and has a longitudinal extension so that it forms sides of those two neighbouring rhombi. Furthermore, the two neighbouring rhombi are rotationally connected via an intermediate revolute joint 6 located between the first and second ends of the connected linkage elements 2 forming sides of those rhombi.

The linkage elements 2 are shaped, dimensioned and arranged so that the axes of all the revolute joints coincide at one common remote centre of motion RCM, so that each of the linkage elements 2 can move on the surface of an imaginary sphere having its centre at the common centre of motion RCM as shown in FIG. 2.a. The dashed lines in the figure show the axes of the revolute joints 5,6 in the illustrated embodiment.

As shown schematically in FIG. 2.a, the curved scissor linkage mechanism 1 is grounded or connected to a first external member 7 via the revolute joint 13 shared with one or both linkage elements 2 arranged at a proximal end 8 of the scissor linkage mechanism and is rotationally connected to a second external member 9 via the revolute joint 14 shared with one or both linkage elements 2 arranged at a distal end 10 of the scissor linkage mechanism 1. The proximal and distal ends 8,10 are those located at opposite ends of the scissor linkage mechanism 1. In the embodiment in FIG. 2, the curved scissor linkage mechanism 1 has a first connector 13 for grounding or connecting the scissor linkage mechanism 1 to the first external member 7 and a second connector 14 for rotationally connecting the scissor linkage mechanism 1 to the second external member 9. The first and second external members 7,9 each connects to one of the linkage elements 2—and thereby the whole scissor linkage mechanism 1—by a connector 13,14. FIG. 2.b shows an alternative shape of the first and second external members 7,9. Which shape and dimensions to use depends on the actual application and how the scissor linkage mechanism is to be connected to other elements.

FIG. 2.c shows an alternative scissor linkage mechanism having the linkage elements 2 forming two parallelograms. This possibility of arranging the linkage elements 2 to form parallelograms instead of rhombi will also apply to at least some of the embodiments in the following figures, including those comprising motion controlling mechanisms.

The curved scissor linkage mechanism 1 is extendable between a fully collapsed configuration and a fully extended configuration. The fully collapsed configuration is shown schematically as seen from two opposite directions in FIGS. 3.a and 3.b. The fully collapsed configuration is shown schematically as seen from two opposite directions in FIGS. 3.c and 3.d.

A curved scissor linkage mechanism 1 according to the invention may also comprise at least one motion controlling mechanism; this will be described in further details below in relation to FIGS. 10 to 14.

Figure 4:
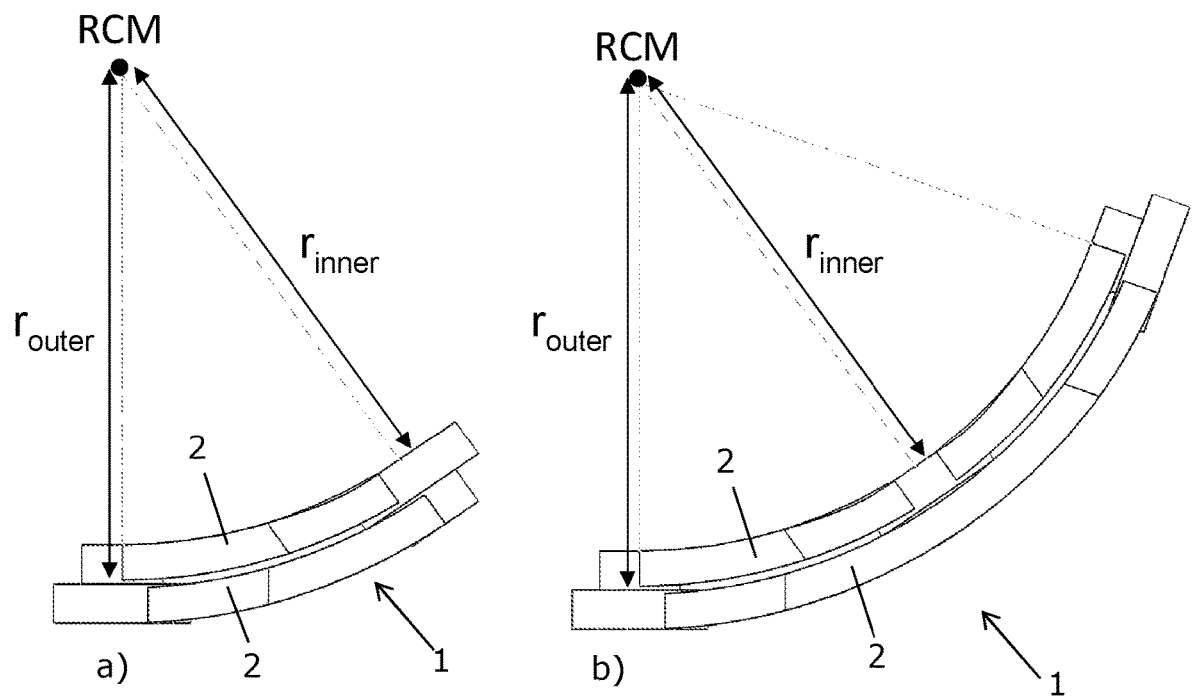
FIG. 4 shows schematically lateral views of linkage elements arranged to move on two imaginary surfaces having different radii of curvature.

The linkage elements 2 of the illustrated embodiments of the invention are arranged in mutually overlapping relationships at the revolute joints 5,6 in such a manner that the linkage elements 2 are movable on two or more imaginary spherical surfaces having different radii of curvature $r_{inner}$ and $r_{outer}$. This is shown schematically in FIG. 4 in which the scissor linkage mechanism 1 is shown in a direction substantially tangentially to the imaginary spherical surfaces on which the linkage elements 2 can move. FIG. 4.a shows a lateral view of the inner and outer small curved linkage elements. The small linkage elements span two revolute joints. The small linkage elements are arranged at the proximal and distal ends of the scissor linkage mechanism. FIG. 4.b shows a lateral view of the inner and outer large curved linkage elements. The large linkage elements span three revolute joints. The large linkage elements are arranged elsewhere, and inner and outer large curved linkage elements cross each other in pairs as seen from the figures. Where they cross, they are joined via intermediate revolute joints 6.

Figure 5:
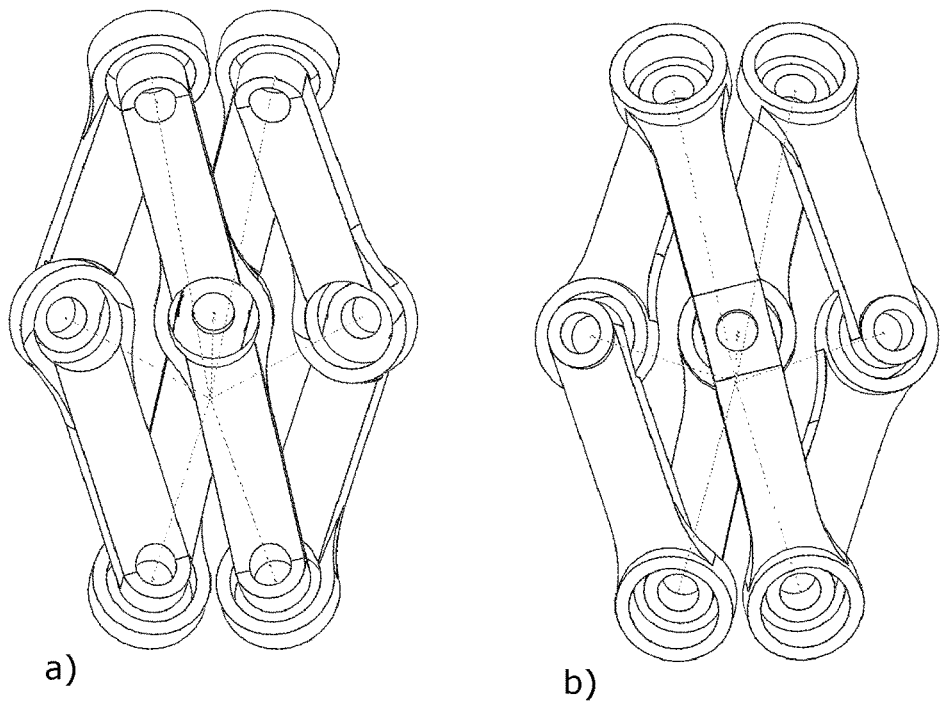
FIG. 5 shows schematically an embodiment of the invention comprising linkage elements with straight sections joined to form coherent rhombi.
Figure 5:
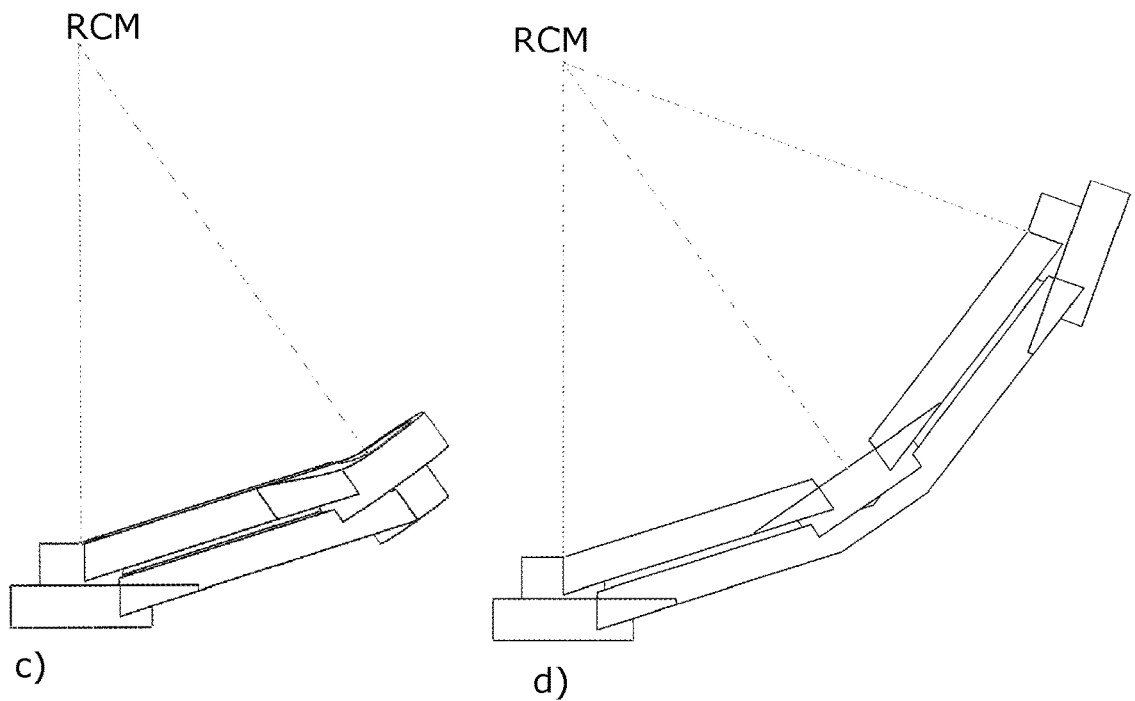

In the embodiments in FIGS. 1 to 4, all the linkage elements are curved. However, it will also be possible to let the scissor mechanism comprise linkage elements with straight sections. An example of such an embodiment is shown schematically in FIG. 5. FIGS. 5.a and 5.b are front and back views, respectively. FIGS. 5.c and 5.d are a lateral view of the inner and outer small linkage elements, and a lateral view of the inner and outer large linkage elements, respectively. For the linkage elements with straight sections, the larger linkage elements need to have a certain angulation regarding its two sections, such that they meet the respective revolute joint that each of these linkages contain.

Figure 6:
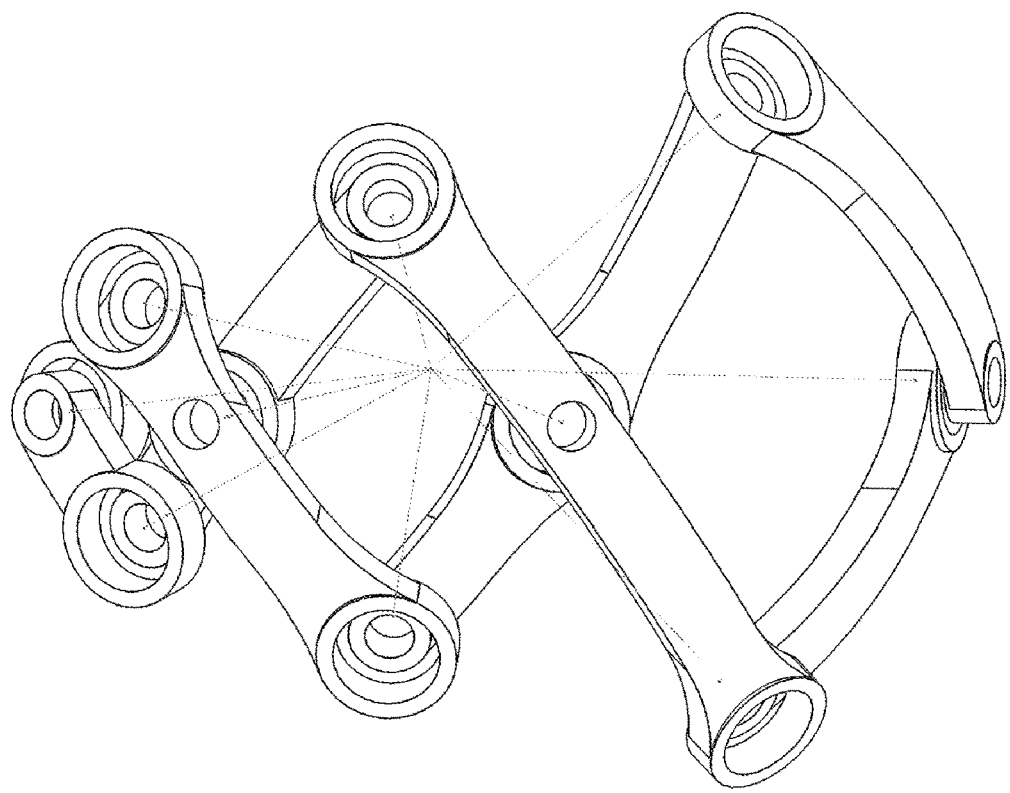
FIG. 6 shows schematically an embodiment of the invention with the linkage elements forming rhombi of different sizes.

In the embodiments shown in most of the previous figures, the dimensions of the linkage elements 2 are so that the rhombi have the same size. However, the scope of the present invention also covers embodiments comprising at least two rhombi of different sizes. FIG. 6 illustrates schematically how the size of the rhombi may be different while mutually opposite angles will be constant. The rhombi need not be arranged in a row of increasing sizes as in FIG. 6.

Figure 7:
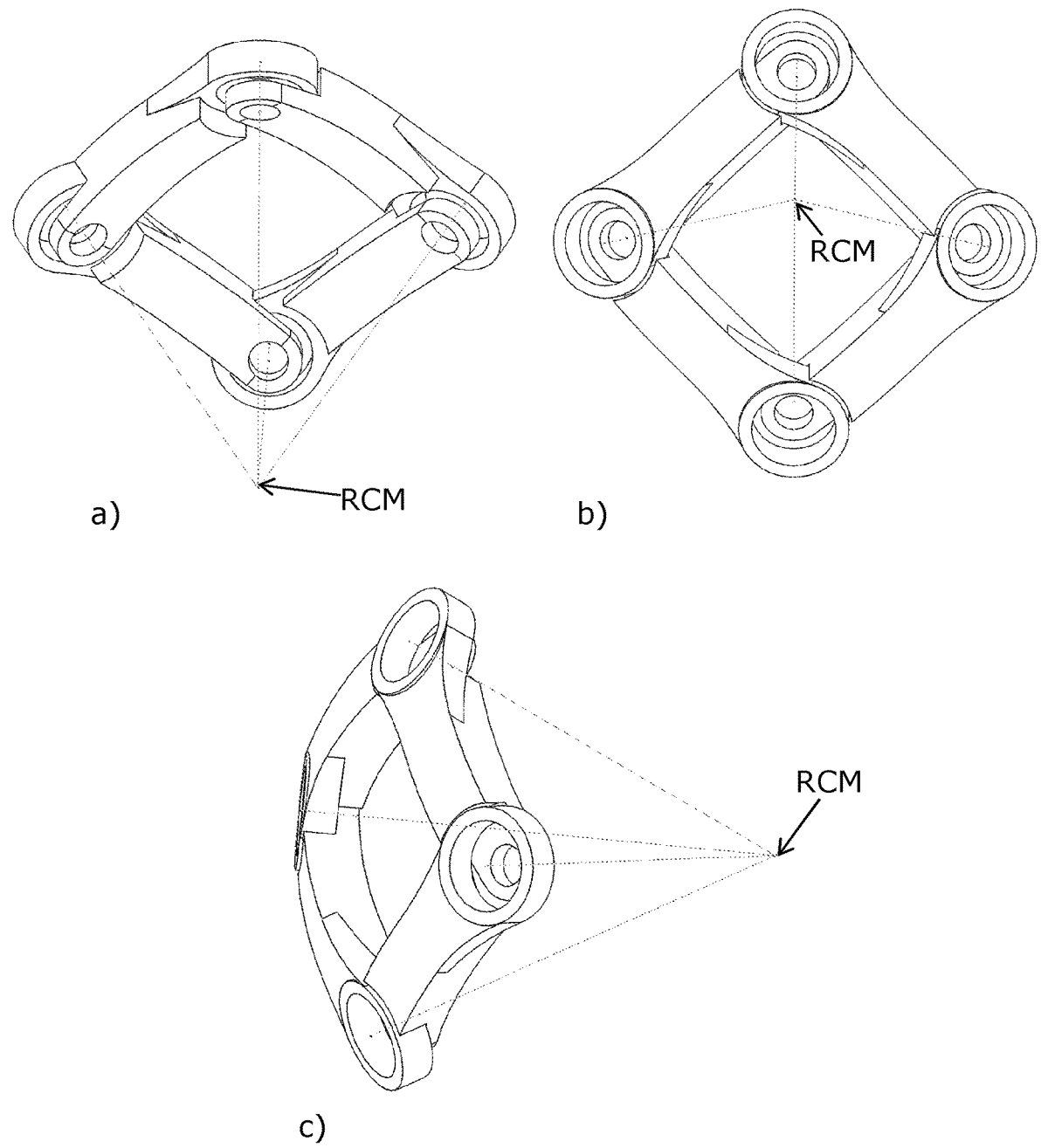
FIG. 7 shows schematically three different views of an embodiment of the invention wherein the linkage elements can move on the same imaginary surface.

For some applications of a scissor linkage mechanism 1 according to the present invention, it may be desired to have all the linkage elements 2 being movable on just one common imaginary spherical surface; this will also be possible within the scope of more radial compactness. FIG. 7 shows schematically such an example wherein the ends of the linkage elements 2 are shaped, dimensioned and arranged in such way that all these elements touch one unique spherical surface.

Figure 8:
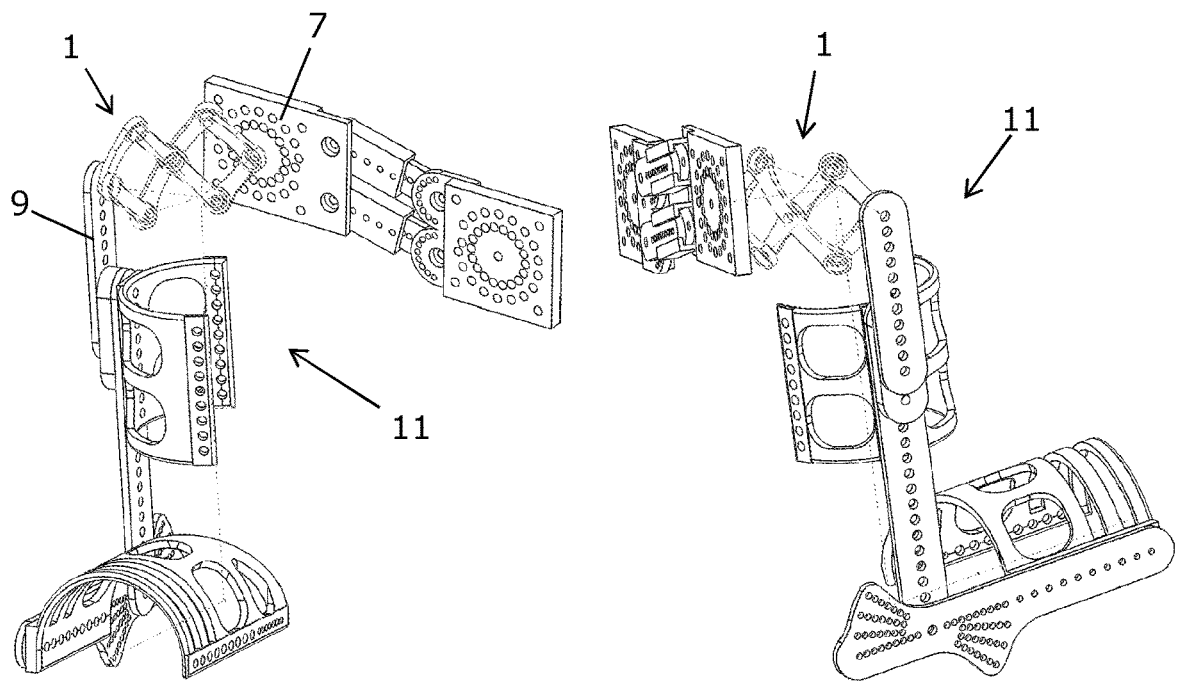
FIG. 8 shows schematically a scissor linkage mechanism according to a first aspect of the invention used in a shoulder joint of an exoskeleton according to a second aspect of the invention.

A potential use of the invention as described above is for an exoskeleton with a joint comprising a curved scissor linkage mechanism 1, such as having the shoulder joints or hip joints made in this way. FIG. 8 shows an exemplary design of a part of an exoskeleton 11 having a shoulder joint designed in accordance with the present invention. The figure also schematically illustrate examples of other elements forming part of a specific exoskeleton build as part of the research done in relation to the present invention. As seen, some of the elements of the exoskeleton 11 are made to be fitted onto a lower and upper part of an upper extremity of the person wearing it. The proximal external component of the mechanism consist of the thorax/trunk attachment, while its second external component is the upper arm segment with a brace. This upper arm brace component is later connected to the lower arm brace by means of a revolute joint matching the anatomical elbow joint. Such an exoskeleton 11 is an example of the use of a curved scissor linkage mechanism 1 according to the present invention for a non-actuated exoskeleton, wherein the mechanism can further comprise actuator means (not shown) for activating the scissor linkage mechanism 1. Such a scissor linkage mechanism 1 may also comprise either control means (not shown) for controlling the actuator means or connectors in communication with external control means for controlling the actuator means.

Figure 9:
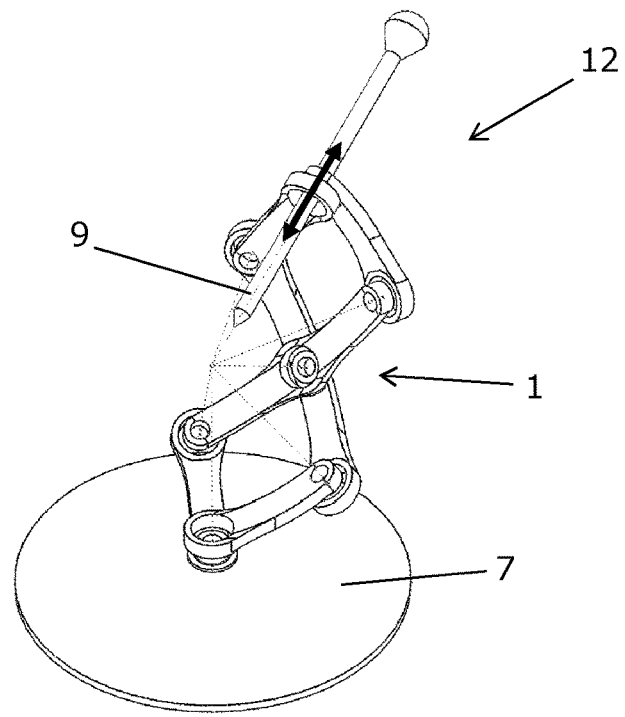
FIG. 9 shows schematically how a scissor linkage mechanism according to the invention can be used in a surgical tool.

FIG. 9 shows schematically a surgical tool 12 comprising a curved scissor linkage mechanism 1 according to the present invention. In this embodiment, the base plate is the first external member 7, and the needle (as a surgery tool example) is the second external member 9 which rotation is neglected but is allowed to translate along that axis. Such a surgical tool may e.g. be used for brain surgery applications where it is an advantage that it can provide access to the brain from all sides.

In the following illustrated embodiments, the motion controlling mechanism at the proximal end 8 is the one used to drive the system while the other one at the distal end 10 is rather driven. For other embodiments, it would be possible to use the motion controlling mechanism at the distal end to drive the system instead. The different parts composing the motion controlling mechanism can also have cable attachment points for controlling purposes, and actuators can be directly applied to them.

FIG. 10 shows schematically an embodiment of a curved scissor linkage mechanism, wherein a motion controlling mechanism 15 is arranged beyond each of the proximal end 8 and the distal end 10. As mentioned above, such a motion controlling mechanism can also be referred to as a motion controlling extension. FIGS. 10.a and 10.b show the curved scissor linkage mechanism as seen from two opposite directions, which could be referred to as a front- and a backside or outer and inner view, respectively. In other embodiments, this type of motion controlling mechanism 15 is arranged beyond one of the ends only. For each of the motion controlling mechanisms 15, the linkage elements 2 at the proximal end 8 or the distal end 10, respectively, are mutually connected at intermediate points 6 so that parts of these linkage elements 2 extend away from the curved scissor linkage mechanism 1. The motion controlling mechanism 15 in this embodiment comprises these extending parts 16 of the linkage elements 2, a guiding member 17 having a guide track 18, and two guide linkage members 19. The guide linkage members 19 are rotationally connected (via a revolute joint) to each other and have a linkage mover 20 arranged at the rotational connection between them. Each of the two guide linkage members 19 rotationally connects one of the extending parts 16 of the linkage elements 2 to the guide track 18. The linkage mover 20 is engaged with the guide track 18 in such a way that the movement of the curved scissor linkage mechanism 1 can be controlled by moving the linkage mover 20 relative to the guide track 18. In the illustrated embodiment, the guide track 18 is in the form of an elongate slot. The scissor linkage mechanism 1 in FIGS. 10.a and 10.b is also provided external members 7 and 9 at both ends.

FIG. 11.b schematically shows a partial view of an embodiment of a curved scissor linkage mechanism, in which a motion controlling mechanism can be observed in detail. FIG. 11.b shows parts of FIG. 10.a as seen from the back side with respect to FIG. 10.a; i.e. part 15 of the mechanism. FIG. 11.a shows parts of FIG. 10.a as seen from above with respect to FIG. 10.a, i.e. parts 2 and 16 of the mechanism. The guiding member has not been included in this figure to more clearly illustrate the difference between curved 2 an planar 16 elements. From FIG. 11.a, it is seen that the linkage elements 2 of the curved scissor linkage mechanism 1 are shaped, dimensioned and arranged so that the axes of all the revolute joints 5 thereof coincide at one common remote centre of motion RCM. In the illustrated embodiment, the motion controlling mechanism 15 is planar, but in other embodiments it can be curved, such as have the same curvature as the linkage elements 2 of the curved scissor linkage mechanism 1, therefore all its revolute joints axes will also coincide at the common remote center of motion RCM.

Figure 12:
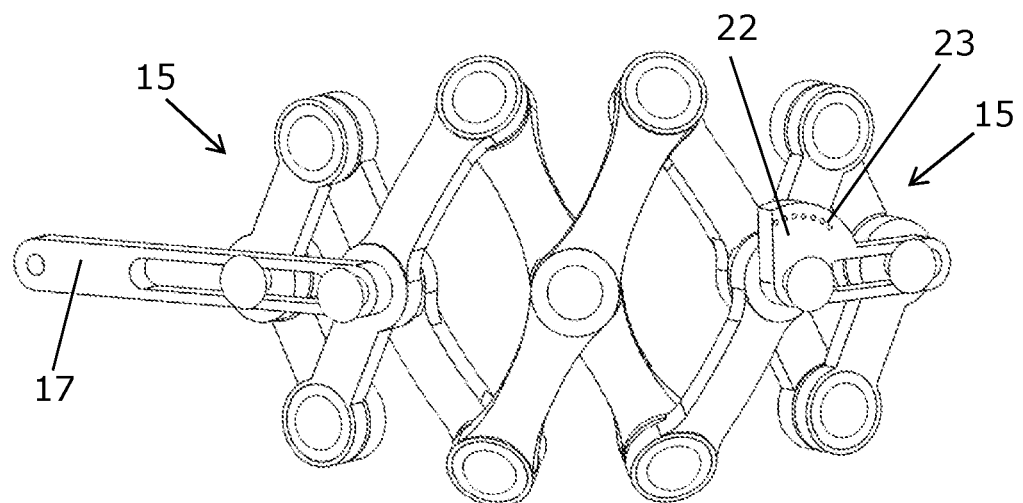
FIG. 12 shows schematically another embodiment of the invention comprising motion controlling mechanisms at both the proximal and distal ends.

FIG. 12 shows schematically an embodiment having motion controlling mechanisms 15 resembling the one in FIG. 10. The guiding members 17 at both proximal and distal ends may have extensions 22 and holes 23 to be used for attachment of e.g. cables (not shown) used for the electric control of the movements of the motion controlling mechanism 15 and the scissor linkage mechanism 1. In the illustrated embodiment, the guiding member at the distal end is provided with a row of holes. Every guiding member 17 can have holes or attachments for cables of an actuation system, if desired, even though such holes are only shown for one of them in the figure.

Figure 13:
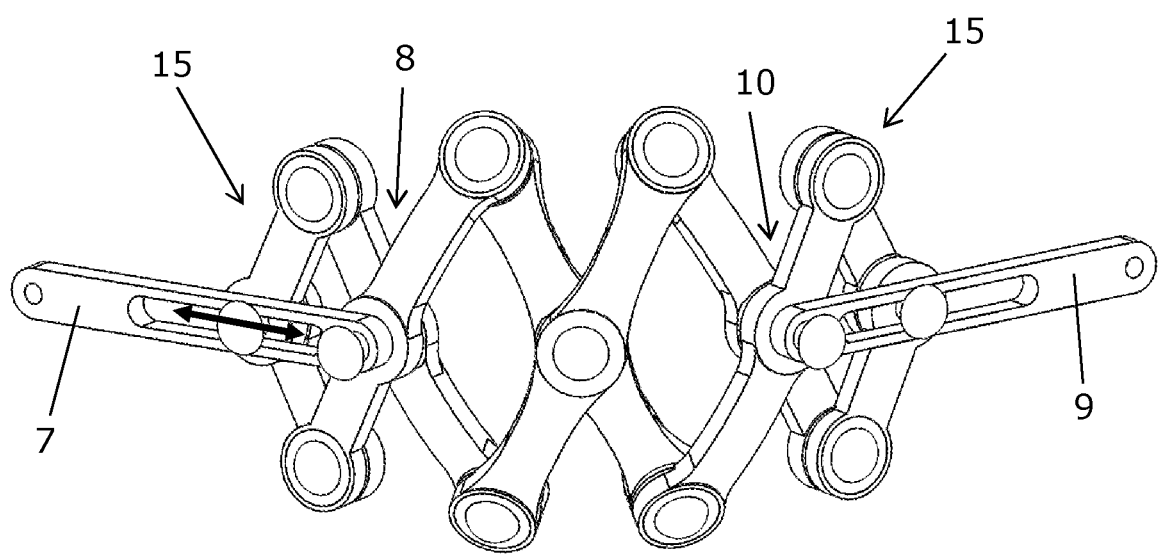
FIGS. 13 and 14 shows schematically two mechanisms in which both external members have a guiding track. The guiding track in FIG. 13 allows the scissor mechanism to fold or extend but not to rotate, while in FIG. 14 the curved guiding track forces the scissor mechanism only to rotate but not to fold or extend.

FIG. 13 shows schematically another mechanism in which both first external member 7 and second external member 9 comprise a guiding track 18 allowing the scissors linkage mechanism 1 only to fold or extend. The other two rotations occurring about the proximal 8 and distal end 10 of the scissor linkage mechanism 1 as shown in FIG. 10.a are cancelled, but for the rest of the figure, the numbering is as in FIG. 10.a. Such an embodiment is another related use of the motion controlling mechanism as a revolute joint. Both external members 7 and 9 are arranged at the proximal end 8 and distal end 10. This mechanism has motion controlling mechanisms 15 arranged at both ends, being one the driver and the other the driven. For this motion controlling mechanism at the proximal end 8, the linkage elements 2 are mutually connected at intermediate points 6 so that parts of these linkage elements extend away from the curved scissor linkage mechanism 1. The motion controlling mechanisms at the distal and proximal ends in FIG. 13 comprise these extending parts of the linkage elements 2 and a linkage mover 20 connected to the guide linkage members 19. In the illustrated embodiment, the first and second external members 7 and 9 composing both proximal and distal motion controlling mechanism comprise guide tracks 18 aligned with the revolute joints 5 between the linkage elements 2 having the extending parts, i.e. at the proximal end 8 and at the distal end 10 of the scissor linkage mechanism 1. The linkage mover is engaged with the guide track in such a way that that folding/extending movement of the curved scissor linkage mechanism 1 can be controlled by moving the linkage mover along the guide track in relation to the external member. Thus, the entire mechanism 1 behaves as a revolute joint having only one degree-of-freedom.

Figure 14:
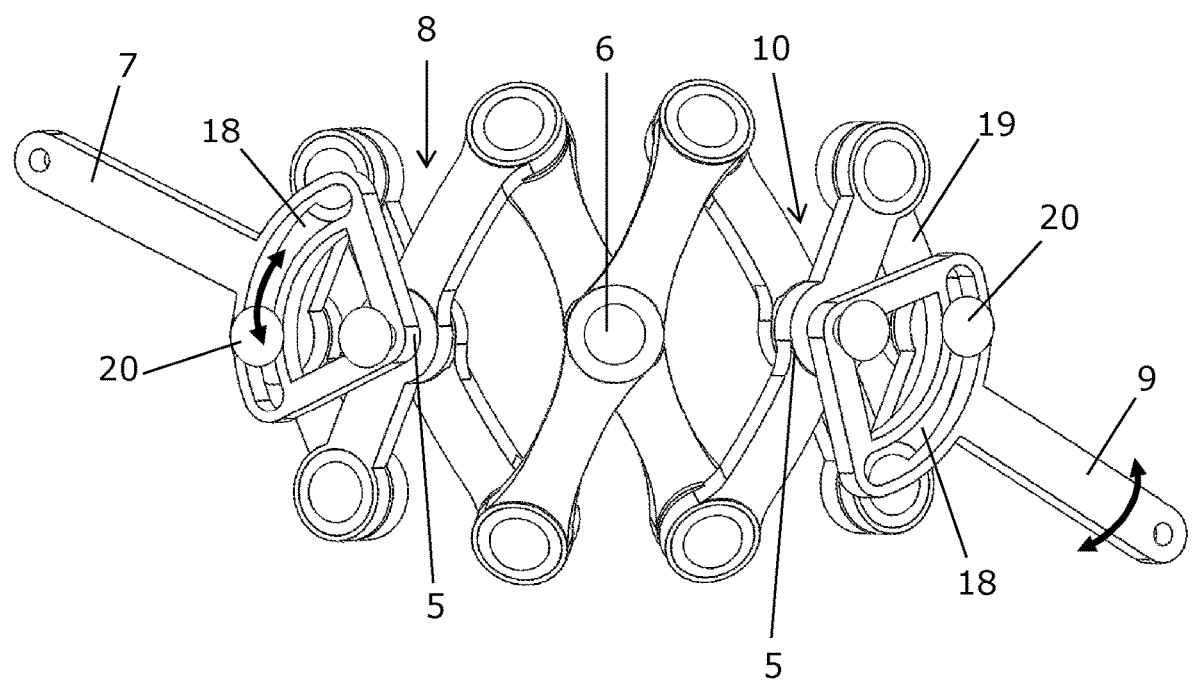

The mechanism in FIG. 14 shows schematically a variation of the embodiment in which the scissor mechanism is prevented from folding or extending by having a motion controlling mechanism at the proximal end, which the driving guiding member is converted as the first external member 7 and has a curved track. For this a motion controlling mechanism at the proximal end 8, the linkage elements 2 are mutually connected at intermediate points 6 so that parts of these linkage elements extend away from the curved scissor linkage mechanism 1. In the illustrated embodiment in FIG. 14, the first external member 7 adjacent to the motion controlling mechanism comprises a curved guide track 18 having a centre of curvature at the revolute joint 5 between the linkage elements 2 having the extending parts 16, i.e. at the proximal end 8 of the scissor linkage mechanism 1. The linkage mover 20 is engaged with the curved guide track in such a way that that rotational movement of the curved scissor linkage mechanism 1 can be controlled by moving the linkage mover 20 in relation to the guide track 18. The radius of the curved guide track 18 defines the constant internal angle at which the scissor mechanism will hold its position, i.e. the angle of how much folded or extended the scissor will constantly be. This embodiment of the scissor linkage mechanism can also include a motion controlling mechanism at the distal end 10 besides having a second external member 9 in the form of a rod (not shown) rotationally arranged at the distal end 10. Thus, this embodiment can have a motion controlling mechanism 15 arranged at the proximal end only. The motion controlling mechanism 15 at the distal end 10 in FIG. 1 comprises these extending parts of the linkage elements 2 and a linkage mover 20 fixedly connected at least one of the extending parts 16 allows to attach cables (not shown) to allow controlling the angular position of a second external member 9. Furthermore, the guiding member of the motion controlling mechanism at the distal end 10 can be directly changed by an external member 9 with a curved guiding track as shown in FIG. 14. This way, the angular rotation of the external element 9 can be controlled by means of actuation anteriorly described. In the following, a more theoretical description will be given to further explain the kinematics of a scissor linkage mechanism according to the invention. In these following sections, what has been referred to as "linkage elements" will be called "linkages". In a planar equilateral parallelogram mechanism, if one of its corners is grounded with a revolute joint, it behaves like a rhombus where its big and small diagonals can alternatively vary their lengths. Such a mechanism has one DOF. If the entire structure can rotate about that grounding revolute joint, then it holds two DOF in total. Lastly, the addition of an extra linkage connected on top of the rhombus, by a revolute joint placed at the opposite vertex of that grounded with a revolute joint, enables a third DOF.

Figure 15:
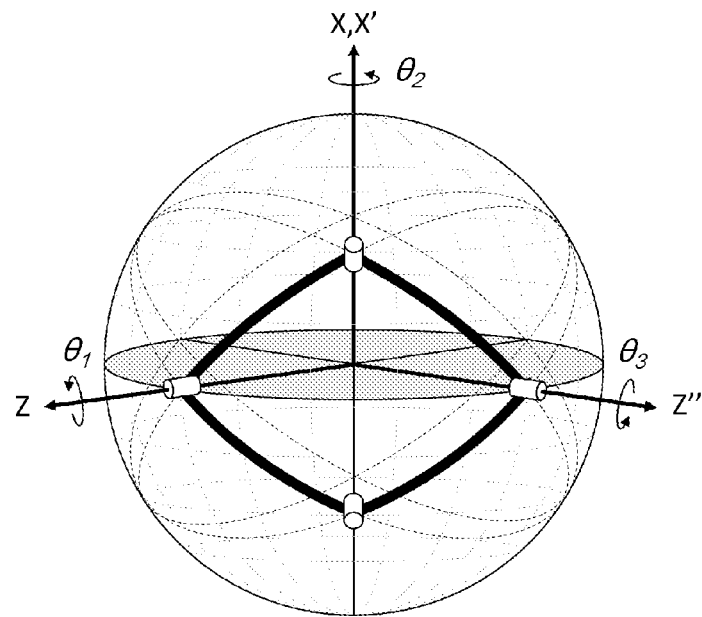
FIG. 15 shows schematically the principle of an embodiment of scissor linkage mechanism with four linkage elements and how it moves on an imaginary spherical surface.

By resorting to curved linkages, with known, constant curvature (fixed radius), all linkages of that rhombus mechanism will move on a spherical surface, as illustrated in FIG. 15. Each linkage describes a great circle arc, between two revolute joints, on a spherical surface. The mechanism is capable of three independent rotations: a yaw angle θ1, a pitch angle θ2 and a roll angle θ3. This occurs since all revolute joints' axes share a common centre of motion (RCM). In a spherical mechanism, a link is characterized by its great circle arc—i.e. the geodesic—between two joints at the sphere centre. Thus, this spherical wrist mechanism with three DOF (a yaw angle $θ_1$, a pitch angle $θ_2$ and a roll angle $θ_3$) is designated as a scissor wrist mechanism (SWR). One of its key features is that its linkages lay and move always on a spherical surface with a pre-defined radius, which is essential to the achievement of a compact design in a spherical wrist mechanism.

Regarding the types of spherical manipulators mentioned earlier, the scissor wrist mechanism should be classified as a serial manipulator even though it comprises crossing links and a closed-loop. Since the mechanism is grounded with a revolute joint, which rotates about the z-axis of the global reference frame as shown in FIG. 15, it has only one fixed point in the global frame. Besides, from this revolute joint, two DOFs are enough to describe the position of the top opposite vertex relative to the grounded vertex, in the rhombus mechanism, in any configuration.

Figure 16:
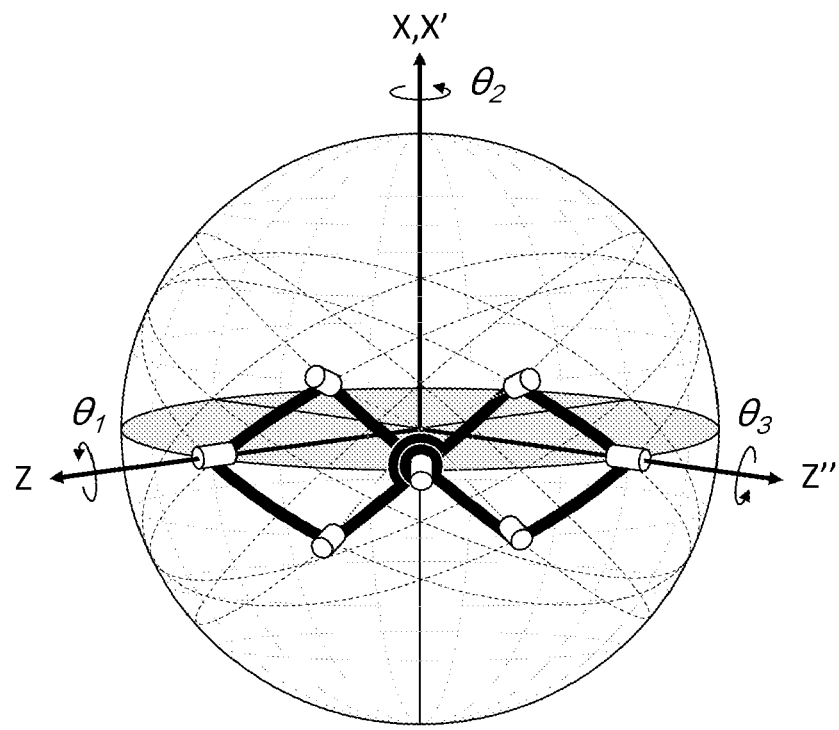
FIG. 16 shows schematically the principle of an embodiment of scissor linkage mechanism with six linkage elements and how it moves on an imaginary spherical surface.

Another possibility for the embodiment of this mechanism is to resort to more than one rhombus in the scissor as exemplified in FIG. 16. In that particular case, the smallest linkages have one-half of the arc length while the longer crossing linkages maintain their original length. This can be of importance in assemblies where it is desired to minimize the spherical area occupied by the mechanism. Particularly, in its folded configuration, the mechanism will tend to protrude on the spherical surface along the circular perimeter of a cross-sectional plane perpendicular to the extension/retraction plane of the scissor wrist mechanism passing through the grounded joint.

Aside from the previous derivation of the kinematics of the spherical gripper mechanism presented in Kocabas, H., 2009, "Gripper Design With Spherical Parallelogram Mechanism". J. Mech. Des. 131, 75001, where a set of projection angles were used around the mechanism's capability of grabbing objects, a new kinematic formulation for this scissor wrist mechanism will be derived showing the ease of driving this mechanism from its base joint like a pure spherical wrist mechanism.

Figure 17:
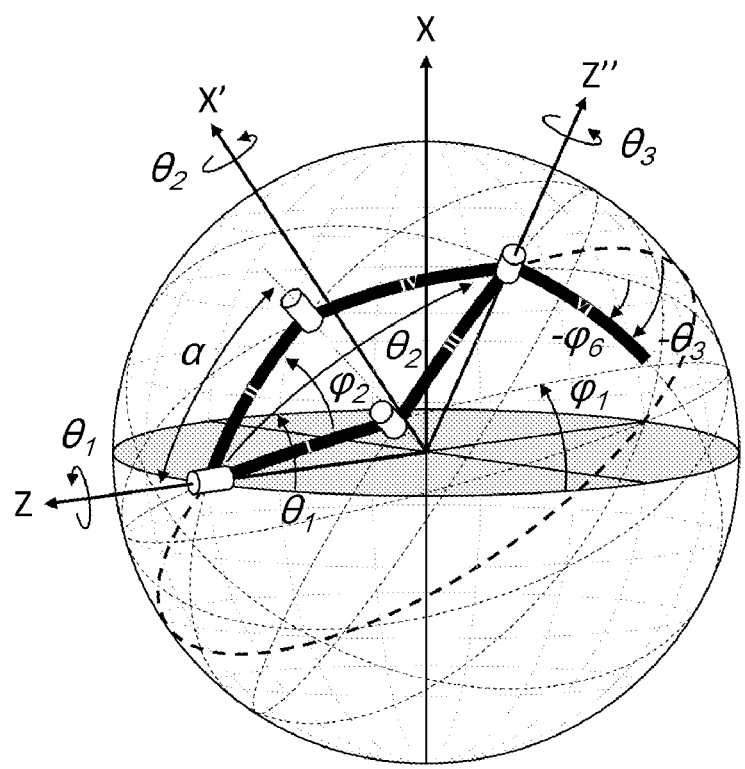
FIG. 17 shows schematically the SWR in terms of its inter-linkage angles and Euler angles.

By choosing the RCM as the common origin for all reference frames of links comprising the mechanism, only rotations are needed to describe how a particular frame moves in relation to another. This helps simplifying the Denavit-Hartenberg angle convention for lower-pairs as radial distances and elevation parameters are not included. Additionally, it has been earlier demonstrated that it is possible to derive the kinematics of a spherical mechanism with a closed loop by separating it into two distinct chains: an upper and a lower chain with even and odd indexing, respectively. That said, the inter-linkage joint angles set $\varphi_i$ and the associated linkages' twist/curvature angles $\alpha_{i-1}$ are presented for the upper chain linkages 2 and 4 of the SWR in FIG. 17 and in Table 1. An extra linkage six is added to represent the rotations of an end-effector link. The z-axis of the reference frame in each linkage points along its proximal revolute joint axes while the x-axis points to the left, perpendicularly to the great circle where that linkage lies (denoted by the dashed lines in FIG. 17). Two angles sets can help describing the kinematics of the mechanism: the inter-linkage joint angles set $\varphi_i$ and an Euler angles set $\theta_j$ following the ZXZ-angle convention. A curvature angle $\alpha$ is associated to each linkage.

The rotation matrix $R_e$, corresponding to the transformation from the end-effector coordinates to the global reference frame, is obtained by consecutive $R_Z$ and $R_X$ rotations about each link's z- and x-axes respectively. This is given by the rotation matrix multiplication sequence shown in Equation (1).

$$R_e = R_Z(\varphi_1) R_Z(\varphi_2) r_X(\alpha) R_Z(-\varphi_2) R_X(\alpha) R_Z(\varphi_6) \quad (1)$$

Another equivalent and simpler expression for $R_e$ can also be found by resorting to a different angles set. Since the scissor wrist mechanism is capable of three sequential rotations, it is possible to find the relation between the joint angles set $\varphi_i$ and three Euler angles $\theta_j$ following the ZXZ-angle convention. This is valuable, for example, to relate the scissor's internal angle $\varphi_2$ with the pitch angle $\theta_2$ of the end-effector of the manipulator. Hence, two of the relations can be directly derived from known angular quantities shown in FIG. 17, while the third relation can be obtained from the spherical law of cosines shown in Equation (2).

TABLE 1

Denavit-Hartenberg parameters of the SWR.

| Link | $\alpha_{i-1}$ | $\varphi_i$ |
|---|---|---|
| 1 | 0 | $\varphi_1$ |
| 2 | 0 | $\varphi_2$ |
| 4 | $\alpha$ | $-\varphi_2$ |
| 6 | $\alpha$ | $\varphi_6$ |

$$\cos\theta_2 = \cos^2\alpha + \sin^2\alpha \cos(\pi - \varphi_2) \quad (2)$$

These relations are described through Equations (3), (4) and (5).

$$\theta_1 = \varphi_1 + \frac{\varphi_2}{2} \quad (3)$$

$$\theta_2 = \arccos(\cos^2\alpha - \sin^2\alpha\cos\varphi_2) \quad (4)$$

$$\theta_3 = \varphi_6 - \frac{\varphi_2}{2} \quad (5)$$

Finally, rotation matrix $R_e$ entries are presented in the following Equation (6), $$R_e = R_Z(\theta_1) R_X(\theta_2) R_Z(\theta_3) = \quad (6)$$

$$\begin{bmatrix} c\theta_1 c\theta_3 - s\theta_1 c\theta_2 s\theta_3 & -c\theta_1 s\theta_3 - s\theta_1 c\theta_2 c\theta_3 & s\theta_1 s\theta_2 \\ s\theta_1 c\theta_3 + c\theta_1 c\theta_2 s\theta_3 & -s\theta_1 s\theta_3 - c\theta_1 c\theta_2 c\theta_3 & -c\theta_1 s\theta_2 \\ s\theta_2 s\theta_3 & s\theta_2 c\theta_3 & c\theta_2 \end{bmatrix}$$

where $c\theta_j$ and $s\theta_j$ correspond to the cosine and sine functions of a $\theta_j$ angle, respectively.

Figure 18:
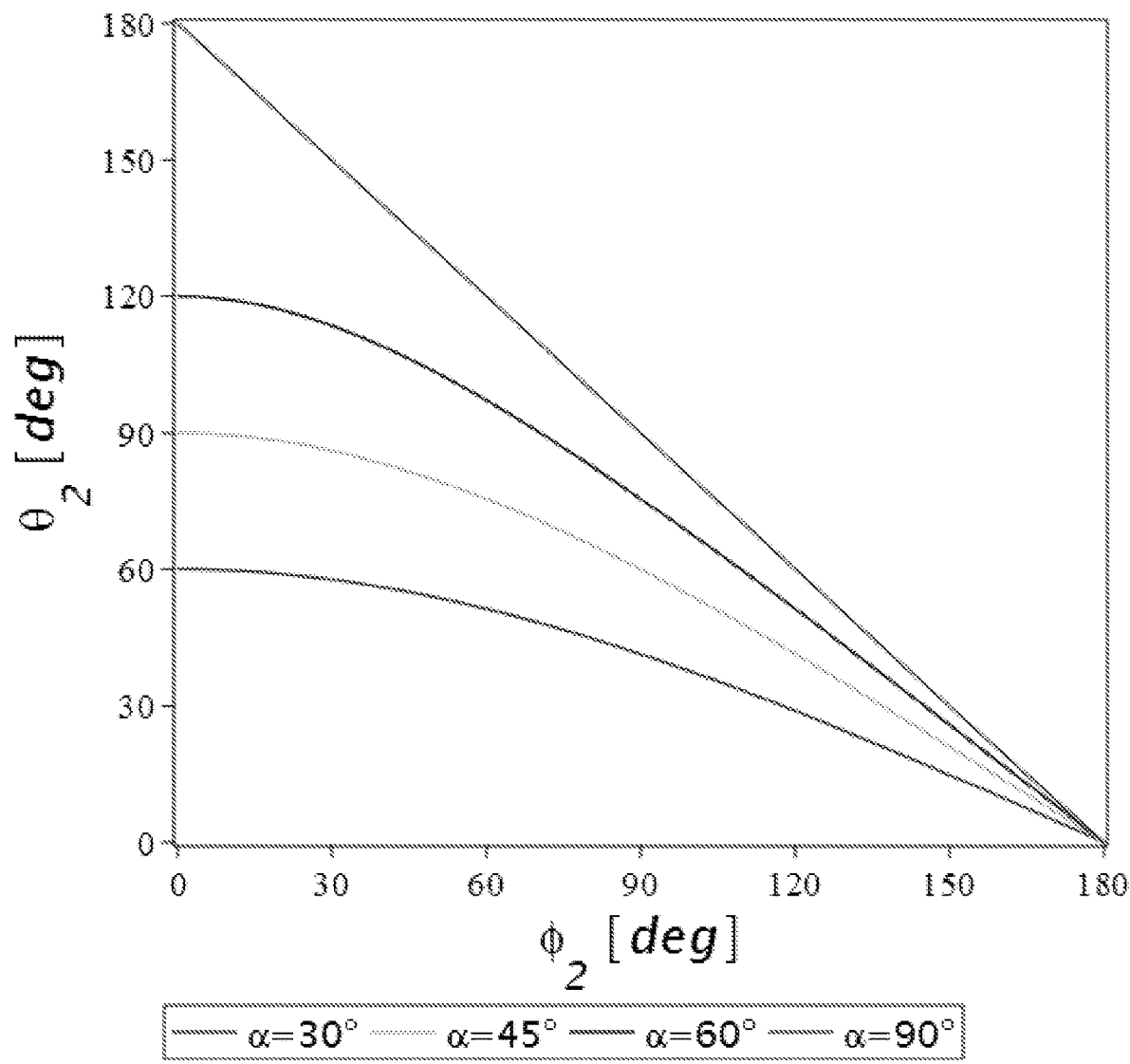
FIG. 18 shows relationships between the end-effector pitch angle and the scissor angle for an embodiment of a scissor linkage mechanism with four linkage elements.

Valuable information can be drawn from the previously mentioned relationships. When plotting the scissor's internal angle $\varphi_2$ with the pitch angle $\theta_2$ of the end-effector (the most distant vertex of the scissor), as plotted in FIG. 18, it is possible to confirm the inverse proportionality between the pitch angle $\theta_2$ and scissor's internal angle $\varphi_2$. FIG. 18 shows the End-effector Pitch Angle—Scissor angle relationship for different values of links curvature angle. On a single rhombus SWM, for a given curvature angle curvature angle $\alpha$ corresponds a pitch angle $\theta_2$ with twice its value. Moreover, for a closed and stretched scissor ($\varphi_2 =$) 0°, the pitch angle $\theta_2$ is twice that of the curvature angle $\alpha$ corresponding to the arc length of each linkage.

Figure 19:
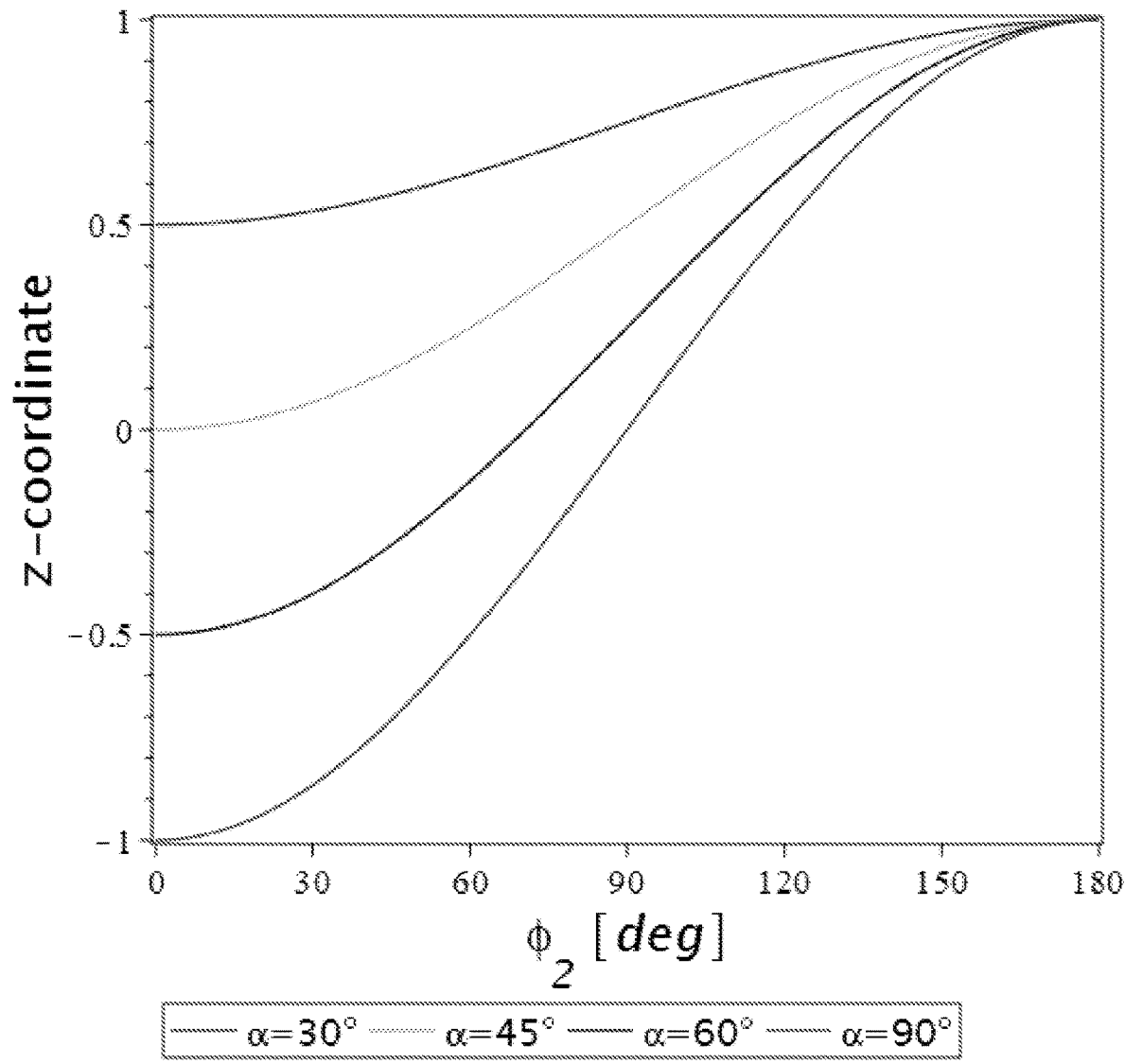
FIG. 19 shows relationships between the end-effector z-value and the scissor angle for an embodiment of a scissor linkage mechanism with four linkage elements.

In a sphere with unitary radius, the relationship between the z-coordinate of the scissor's end-effector in the global reference frame and the scissor's internal angle $\varphi_2$ is given by the cosine of the pitch angle $\theta_2$. This is represented in FIG. 19 and one can observe a central region in the domain where the relation between the two variables can be approximated by a linear function. FIG. 19 illustrates the End-effector z-value—Scissor Angle relationship for different values of links curvature angle $\alpha$. A central region shows a linear behaviour between both variables.

The inverse problem consists of computing the three Euler angles $\theta_j$ from a given final positions of the end-effector of the manipulator. This can be achieved by initially calculating the value of the pitch angle $\theta_2$ directly from the last entry of the rotation matrix $R_e$ as in Equation (7). The $r_{ij}$ represents the matrix element in the $i^{th}$ row and $j^{th}$ column. Since the mechanism operates in the range of $\theta_2 \in [0, 2\alpha]$, only the positive angle from Equation (7) is of interest.

$$\cos(\theta_2) = r_{33} \quad (7)$$

Once the pitch angle $\theta_2$ is known, the remaining elements in the last row and last column of the rotation matrix $R_e$ can be paired in terms of the remaining $\theta_1$ and $\theta_3$ angles and trivially obtained by resorting to the geometrical tangent function as in Equations (8) and (9).

$$\theta_1 = \arctan 2(r_{13}/s\theta_2, -r_{23}/s\theta_2) \quad (8)$$

$$\theta_3 = \arctan 2(r_{31}/s\theta_2, r_{32}/s\theta_2) \quad (9)$$

In case the main goal is, then, to obtain the mechanism's joint angles $\varphi_i$, one can simply use the previously mentioned Equations (3), (4) and (5).

A manipulator's Jacobian matrix $J(\theta)$ relates the mechanism's joint velocities $\dot{\theta}$ with the angular velocity $\omega_e$ of its last reference frame, i.e. the angular velocity of its end-effector—as described by Equation (10). From the analysis of the mechanism's Jacobian matrix, one can evaluate its performance through its manipulability measure w.

$$\omega_e = J(\theta)\dot{\theta} \quad (10)$$

For the current set of ZXZ Euler angles, the generalized velocity vector is $\dot{\theta} = [\dot{\theta}_1 \ \dot{\theta}_2 \ \dot{\theta}_3]^T$, while the end-effector angular-velocity vector is $\omega_e = [\omega_x \ \omega_y \ \omega_z]^T$.

According to Euler's rotation theorem, any sequence of rotations can be described by a unit vector $\hat{k}$—the instantaneous axis of rotation—which is then scaled by the amount of rotation $\theta$ about that same axis. The theorem can then be extended such that, at any time instant, the angular-velocity vector $\omega_e$ is equal to the speed of rotation $\dot{\theta}$ about that same instantaneous axis of rotation $\hat{k}$—see equation (11).

$$\omega_e = \dot{\theta}\hat{k} \quad (11)$$

Likewise, the angular-velocity vector $\omega_e$ can be derived from the skew-symmetric matrix S of the angular velocities for the particular rotation matrix $R_e$ of the mechanism. This is achieved by solving the matrix Equation (12), which corresponds to the three independent Equations (13), (14) and (15).

$$S = \dot{R}_e R_e^T = \begin{bmatrix} 0 & -\omega_z & \omega_y \\ \omega_z & 0 & -\omega_x \\ -\omega_y & \omega_x & 0 \end{bmatrix} \quad (12)$$

$$\omega_x = \dot{r}_{31}r_{21} + \dot{r}_{32}r_{22} + \dot{r}_{33}r_{23} \quad (13)$$

$$\omega_y = \dot{r}_{11}r_{31} + \dot{r}_{12}r_{32} + \dot{r}_{13}r_{33} \quad (14)$$

$$\omega_z = \dot{r}_{21}r_{11} + \dot{r}_{22}r_{12} + \dot{r}_{23}r_{13} \quad (15)$$

By solving these equations for the generalized velocity vector $\dot{\theta}$, it is then possible to obtain the following Jacobian matrix $J(\theta)$ for the mechanism—Equation (16).

$$J(\theta) = \begin{bmatrix} 0 & c\theta_1 & s\theta_1 s\theta_2 \\ 0 & s\theta_1 & -c\theta_1 s\theta_2 \\ 1 & 0 & c\theta_2 \end{bmatrix} \quad (16)$$

The manipulability, w, accesses whether the maximum rank of the Jacobian matrix is, at a given point, lower than the number of DOFs of the mechanism. It can also be understood as the capability of the mechanism to arbitrarily change both position and orientation of its end-effector. In the case the rank is lower than the number of DOFs for a given joint configuration, the determinant of the Jacobian matrix is null and meaning that the mechanism reached a singular point. This is reflected through the following Equation (17), involving the determinant of the Jacobian multiplied by its transpose. If w is zero for a given configuration in the joint space $\theta$, that configuration is said to be a singular.

$$w = \sqrt{\det(J(\theta)J^T(\theta))} = |\det(J(\theta))| = |s\theta_2| \quad (17)$$

The result of Equation (17) confirms that the singularities of the mechanism are only dependent on the pitch angle $\theta_2$ and occur at the points where the first and last rotation axes are aligned. Such singularities correspond to any completely folded scissor configuration ($\theta_2 = 0°$, $\varphi_2 = 180°$) and to the fully stretched scissor configuration when the linkage's curvature angle is $\alpha = 90°$ ($\theta_2 = 180°$, $\varphi_2 = 0°$). In theory, for designing a singularity-free scissor wrist mechanism, this results in the following general design Equation (18) relating the maximum pitch angle $\theta_2^{max}$ with the chosen linkages' curvature angle $\alpha$ and the n number of rhombi in the mechanism.

$$\theta_2^{max} = 2\alpha n < 180°, n \in \mathbb{N} \quad (18)$$

Figure 20:
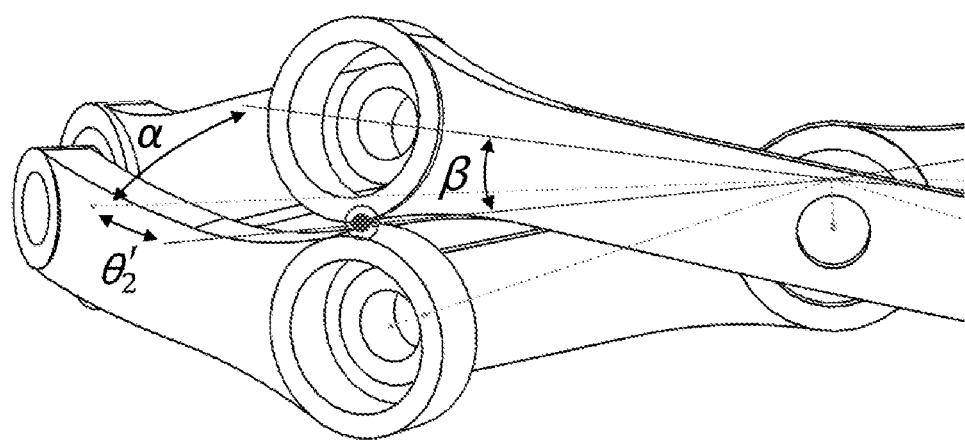
FIG. 20 shows schematically the maximum extended configuration of scissor linkage mechanism illustrating the collision point.

From a practical point of view, the joint and linkages of the mechanism do not behave as punctual neither line entities. This means that on a real manufactured mechanism, material exists around each joint axes, for example, to accommodate bearings. In addition, the bearings themselves take some of the effective spherical surface on which the mechanism works. As illustrated in FIG. 15, as the mechanism reaches its singular configurations, the boundaries of the parts composing the scissor wrist will collide. This naturally occurs for both situations mentioned above, of the most folded and most stretched scissor configurations. FIG. 20 shows the maximum stretched configuration of the SWR illustrating the collision point (marked with bold). An intrusive angle $\beta$ is defined as the angle from the joint axis to an axis passing through that collision point. The spherical law of cosines enables relating the intrusive angle $\beta$ with the curvature angle $\alpha$ and the portion of the scissor's pitch angle $\theta_2'$ between the base joint and the collision point. An intrusive angle $\beta$ is defined as the angle from the joint axis to an imaginary axis tangential to the furthest point composing the joint. That allows defining the real mechanism's angular limits in its most stretched configuration by resorting to the spherical law of cosines as in Equation (2). Since the plane where intrusive angle $\beta$ sits is perpendicular to the pitch angle $\theta_2$ plane, the spherical law of cosines is simplified to Equation (19) as all its sine terms are null.

$$\cos \theta_2' = \cos \alpha / \cos \beta \quad (19)$$

where $\theta_2'$ represents the portion of the scissor's pitch angle spanned between the mechanism's base joint axis and the tangential imaginary axis from which the intrusive angle $\beta$ is measured. Thus, the maximum pitch angle is effectively $\theta_2^{max} = 2n\theta_2'$. On the other hand, by reasoning on the same intrusive angle $\beta$ for the most folded configuration, the minimum pitch angle is $\theta_2^{min} = 2n\beta$. Such feature of preventing the mechanism from reaching any singularity configuration grants stability, which is suitable for shoulder mechanisms.

The scissor wrist's spherical coordinate space, as opposed to the Cartesian coordinate space of most robotic manipulators, makes this mechanism suitable for certain applications, such as spherical coordinate positioning tools for instance in the medical field, where the currently available robots for minimally invasive surgery tend to require large spaces. Many of these surgery tools are required to be confined to a small space, such as that of an imaging scanner, when performing intraoperative navigation. The spherical scissor wrist can potentially provide a stiff surgical support tool which could otherwise only be achieved by larger, parallel robots. Other potential application areas are 3d-printing, haptic devices, laser welding/cutting tools and camera inspection structures for quality control, but all of these potential applications require further investigation.

Studies on exoskeletons made in relation to the development of the present invention have shown that it is possible to obtain that the only singularities in the human shoulder for the analysed scissor linkage mechanism with near full workspace occur both at 90 degrees of shoulder internal ($\theta_2 \approx 180°$, $\varphi_2=0°$) and external ($\theta_2=0°$, $\varphi_2=180°$) rotations. The first is not attainable since it would mean penetrating the torso, while the second corresponds to a point near the human upper extremity reachable workspace and typically not reached by any activity of the daily living. After manufacturing and testing the prototype of the scissor wrist mechanism it was possible to confirm a good fitting to the shoulder anatomy.

The prototype which was manufactured during the studies showed that having an intrusive angle help on avoiding the fully folded and fully stretched scissor configurations, granting stability to the mechanism. The exclusive use of revolute joints may represent an advantage from a fabrication point-of-view, in the sense that revolute joints can be realised with standard bearings of low cost and high reliability.

Although the present invention has been described in connection with the specified embodiments, it should not be construed as being in any way limited to the presented examples. The scope of the present invention is set out by the accompanying claim set. In the context of the claims, the terms "comprising" or "comprises" do not exclude other possible elements or steps. In addition, the mentioning of references such as "a" or "an" etc. should not be construed as excluding a plurality. The use of reference signs in the claims with respect to elements indicated in the figures shall also not be construed as limiting the scope of the invention. Furthermore, individual features mentioned in different claims, may possibly be advantageously combined, and the mentioning of these features in different claims does not exclude that a combination of features is not possible and advantageous.

The invention claimed is:

1. A curved scissor linkage mechanism, comprising:
   at least four linkage elements each having a first end and a second end, the linkage elements being arranged to form sides of at least one rhombus or of at least one parallelogram, wherein
   the curved scissor linkage mechanism is extendable between a fully collapsed configuration and a fully extended configuration,
   each of the linkage elements
      is rotationally connected to at least one of the other linkage elements via a revolute joint at or near the first end and/or at an intermediate point between the first end and the second end, and
      is rotationally connected to at least another one of the other linkage elements via another revolute joint at or near the second end and/or at an intermediate point between the first end and the second end, and
   the linkage elements are shaped, dimensioned and arranged so that the axes of all said revolute joints coincide at one common remote centre of motion (RCM), so that each of the linkage elements can move on the surface of an imaginary sphere having its centre at the common centre of motion (RCM), and
   the curved scissor linkage mechanism is connected to a first external member via the revolute joint between linkage elements arranged at a proximal end of the curved scissor linkage mechanism and is rotationally connected to a second external member via the revolute joint between linkage elements arranged at a distal end of the curved scissor linkage mechanism, the proximal and distal ends being located at opposite ends of the scissor linkage mechanism.

2. The curved scissor linkage mechanism according to claim 1, wherein a motion controlling mechanism is arranged at the proximal end and/or at the distal end, and wherein for each motion controlling mechanism:
   the linkage elements at the proximal end or the distal end, respectively, are mutually connected at intermediate points so that parts of these linkage elements extend away from the curved scissor linkage mechanism,
   the motion controlling mechanism comprises the extending parts of the linkage elements, and
   the movement of the curved scissor linkage mechanism can be controlled by moving the two extending parts of the linkage elements.

3. The curved scissor linkage mechanism according to claim 2, wherein the motion controlling mechanism further comprises:
   a guiding member having a guide track, and
   two guide linkage members which are rotationally connected to each other and have a linkage mover arranged at the rotational connection between them,
   wherein each of the two guide linkage members rotationally connects one of the extending parts of the linkage elements to the linkage mover, and
   wherein the linkage mover is engaged with the guide track in such a way that the movement of the curved scissor linkage mechanism can be controlled by moving the linkage mover relative to the guide track, or by moving directly the two extending parts of the linkage elements at the proximal end and/or the distal end.

4. The curved scissor linkage mechanism according to claim 2, wherein:
   the motion controlling mechanism further comprises a linkage mover connected to at least one of the extending parts via a guide linkage member,
   the first or the second external member adjacent to the motion controlling mechanism comprises a guide track, and
   the linkage mover is engaged with the guide track in such a way that the movement of the curved scissor linkage mechanism can be controlled by moving the linkage mover in relation to the guide track.

5. The curved scissor linkage mechanism according to claim 1, further comprising a first connector for grounding or connecting the scissor linkage mechanism to the first external member and/or a second connector for rotationally connecting the scissor linkage mechanism to the second external member.

6. The curved scissor linkage mechanism according to claim 1, comprising at least six linkage elements arranged to form a series of at least two coherent rhombi, wherein:
   each of the linkage elements located adjacent to a subsequent rhombus is shared by two neighbouring rhombi and has a longitudinal extension so that it forms sides of those two neighbouring rhombi, and
   neighbouring rhombi are rotationally connected via an intermediate revolute joint located between the first and second ends of the connected linkage elements forming sides of those rhombi.

7. The curved scissor linkage mechanism according to claim 1, comprising at least six linkage elements arranged to form a series of at least two coherent parallelograms, wherein:
- each of the linkage elements located adjacent to a subsequent parallelogram is shared by two neighbouring parallelograms and has a longitudinal extension so that it forms sides of those two neighbouring parallelograms, and
- neighbouring parallelograms are rotationally connected via an intermediate revolute joint located between the first and second ends of the connected linkage elements forming sides of those parallelograms.

8. The curved scissor linkage mechanism according to claim 1, wherein all the linkage elements are curved.

9. The curved scissor linkage mechanism according to claim 1, wherein the linkage elements are arranged in mutually overlapping relationships at the revolute joints in such a manner that the linkage elements are movable on two or more imaginary spherical surfaces having different radii of curvature.

10. The curved scissor linkage mechanism according to claim 1, wherein the linkage elements are shaped, dimensioned and arranged in such a way at the first and second ends that all the linkage elements are movable on one common imaginary spherical surface.

11. The curved scissor linkage mechanism according to claim 1, comprising at least two rhombi or parallelograms of different sizes.

12. The curved scissor linkage mechanism according to claim 1, further comprising
- actuator means for activating the scissor linkage mechanism, and
- either control means for controlling the actuator means or connectors in communication with external control means for controlling the actuator means.

13. An exoskeleton with a joint comprising a curved scissor linkage mechanism according to claim 1.

14. The exoskeleton according to claim 13, wherein the joint is a shoulder joint or a hip joint.

15. A spherical coordinate positioning tool comprising a curved scissor linkage mechanism according to claim 1.

16. The spherical coordinate positioning tool according to claim 15, wherein the tool is a surgical tool.

\* \* \* \* \*